(12) United States Patent
Pappas et al.

(10) Patent No.: US 7,637,935 B2
(45) Date of Patent: Dec. 29, 2009

(54) ENDOPROSTHESIS FOR CONTROLLED CONTRACTION AND EXPANSION

(75) Inventors: Jeff Pappas, Santa Clara, CA (US); Anton G. Clifford, Mountain View, CA (US); Brett Cryer, Sunnyvale, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/430,636

(22) Filed: May 6, 2003

(65) Prior Publication Data

US 2004/0093072 A1    May 13, 2004

Related U.S. Application Data

(60) Provisional application No. 60/378,278, filed on May 6, 2002, provisional application No. 60/378,279, filed on May 6, 2002, provisional application No. 60/378,345, filed on May 8, 2002, provisional application No. 60/379,310, filed on May 8, 2002.

(51) Int. Cl.
*A61F 2/06* (2006.01)
(52) U.S. Cl. ................................. 623/1.12; 623/1.15
(58) Field of Classification Search ................. 623/1.12, 623/1.15
See application file for complete search history.

(56) References Cited

U.S. PATENT DOCUMENTS

| | | | |
|---|---|---|---|
| 3,561,102 A | 2/1971 | Diemer | |
| 4,503,569 A | 3/1985 | Dotter | |
| 4,580,568 A | 4/1986 | Gianturco | |
| 4,830,003 A | 5/1989 | Wolff et al. | |
| 4,856,516 A | 8/1989 | Hillstead | |
| 5,102,417 A | 4/1992 | Palmaz | |
| 5,104,404 A | 4/1992 | Wolff | |
| 5,356,423 A | 10/1994 | Tihon et al. | |
| 5,403,341 A | 4/1995 | Solar | |
| 5,449,373 A | 9/1995 | Pinchasik et al. | |
| 5,540,713 A | 7/1996 | Schnepp-Pesch et al. | |
| 5,591,223 A | 1/1997 | Perry et al. | |
| 5,601,593 A | 2/1997 | Freitag | |
| 5,607,442 A | 3/1997 | Fischell et al. | |

(Continued)

FOREIGN PATENT DOCUMENTS

CA    2512311 A1 * 11/1995

(Continued)

*Primary Examiner*—Corrine M McDermott
*Assistant Examiner*—Christopher D Prone
(74) *Attorney, Agent, or Firm*—Baker Botts L.L.P.

(57) ABSTRACT

An endoprosthesis that has an interconnected series of struts, selected strut members connected to adjacent strut members at a longitudinal apex. Strut members include a first end portion, an intermediate portion hingedly connected to the first end portion, and a second end portion hingedly connected to the intermediate portion and extending to the apex. Some of the strut members can have a nesting feature configured for nestingly receiving another strut member when the endoprosthesis is in the delivery condition. A scaffolding body of the endoprosthesis can have an inner and outer component, each having a set of interconnected strut members which overlap those of the other to define a cooperating cell pattern. Also, the endoprosthesis can be configured to naturally tend to contract when the body is smaller than a predetermined diameter and expand when the body is larger than a predetermined diameter.

13 Claims, 15 Drawing Sheets

U.S. PATENT DOCUMENTS

| | | | |
|---|---|---|---|
| 5,697,971 | A | 12/1997 | Fischell et al. |
| 5,725,572 | A | 3/1998 | Lam et al. |
| 5,755,771 | A | 5/1998 | Penn et al. |
| 5,776,162 | A | 7/1998 | Kleshinski |
| 5,810,868 | A | 9/1998 | Lashinski et al. |
| 5,817,152 | A | 10/1998 | Birdsall et al. |
| 5,853,419 | A | 12/1998 | Imran |
| 5,858,556 | A | 1/1999 | Eckert et al. |
| 5,860,999 | A | 1/1999 | Schnepp-Pesch et al. |
| 5,902,317 | A | 5/1999 | Kleshinski |
| 5,911,754 | A | 6/1999 | Kanesaka et al. |
| 5,913,895 | A | 6/1999 | Burpee et al. |
| 5,922,020 | A | 7/1999 | Klein et al. |
| 5,928,280 | A | 7/1999 | Hansen et al. |
| 5,938,682 | A | 8/1999 | Hojeibane |
| 5,938,697 | A | 8/1999 | Killion et al. |
| 6,017,365 | A | 1/2000 | Von Oepen |
| 6,027,526 | A | 2/2000 | Limon et al. |
| 6,027,528 | A | 2/2000 | Tomonto et al. |
| 6,033,433 | A * | 3/2000 | Ehr et al. .................... 623/1.16 |
| 6,042,606 | A | 3/2000 | Frantzen et al. |
| 6,053,940 | A | 4/2000 | Wijay |
| 6,053,941 | A | 4/2000 | Lindenberg et al. |
| 6,068,656 | A | 5/2000 | Von Oepen |
| 6,090,127 | A | 7/2000 | Globerman |
| 6,099,561 | A | 8/2000 | Alt |
| 6,113,627 | A | 9/2000 | Jang |
| 6,129,754 | A | 10/2000 | Kanesaka et al. |
| 6,136,023 | A | 10/2000 | Boyle |
| 6,183,507 | B1 | 2/2001 | Lashinski et al. |
| 6,190,406 | B1 | 2/2001 | Duerig et al. |
| 6,193,744 | B1 | 2/2001 | Ehr et al. |
| 6,193,747 | B1 | 2/2001 | Von Oepen |
| 6,200,334 | B1 | 3/2001 | Jang |
| 6,206,911 | B1 | 3/2001 | Milo |
| 6,217,608 | B1 * | 4/2001 | Penn et al. ................. 623/1.16 |
| 6,231,598 | B1 | 5/2001 | Berry et al. |
| 6,241,757 | B1 | 6/2001 | An et al. |
| 6,245,100 | B1 | 6/2001 | Davila et al. |
| 6,253,443 | B1 | 7/2001 | Johnson |
| 6,258,117 | B1 | 7/2001 | Camud et al. |
| 6,270,524 | B1 | 8/2001 | Kim |
| 6,287,336 | B1 | 9/2001 | Globerman et al. |
| 6,290,720 | B1 | 9/2001 | Khosravi et al. |
| 6,299,635 | B1 | 10/2001 | Frantzen |
| 6,309,414 | B1 | 10/2001 | Rolondo et al. |
| 6,315,794 | B1 | 11/2001 | Richter |
| 6,331,189 | B1 | 12/2001 | Wolinsky et al. |
| 6,334,870 | B1 | 1/2002 | Ehr et al. |
| 6,340,366 | B2 | 1/2002 | Wijay |
| 6,342,067 | B1 | 1/2002 | Mathis et al. |
| 6,344,053 | B1 | 2/2002 | Boneau |
| 6,348,065 | B1 | 2/2002 | Brown et al. |
| 6,350,277 | B1 | 2/2002 | Kocur |
| 6,352,552 | B1 | 3/2002 | Levinson et al. |
| 6,355,827 | B1 | 3/2002 | Komoschinski et al. |
| 6,416,543 | B1 | 7/2002 | Hilaire et al. |
| 6,423,084 | B1 | 7/2002 | St. Germain |
| 6,423,090 | B1 | 7/2002 | Hancock |
| 6,428,570 | B1 | 8/2002 | Globerman |
| 6,432,133 | B1 | 8/2002 | Lau et al. |
| 6,443,982 | B1 | 9/2002 | Israel et al. |
| 6,451,052 | B1 | 9/2002 | Burmeister et al. |
| 6,475,236 | B1 | 11/2002 | Roubin et al. |
| 6,475,239 | B1 | 11/2002 | Campbell et al. |
| 6,485,508 | B1 * | 11/2002 | McGuinness ............... 623/1.15 |
| 6,511,505 | B2 | 1/2003 | Cox et al. |
| 6,558,415 | B2 | 5/2003 | Thompson |
| 2001/0000043 | A1 | 3/2001 | Israel |
| 2001/0000188 | A1 | 4/2001 | Cox et al. |
| 2001/0014822 | A1 | 8/2001 | Milo |
| 2001/0027339 | A1 | 10/2001 | Brummett et al. |
| 2001/0044648 | A1 | 11/2001 | Wolinsky et al. |
| 2001/0044653 | A1 | 11/2001 | Kveen et al. |
| 2001/0047200 | A1 | 11/2001 | White |
| 2002/0007212 | A1 | 1/2002 | Brown et al. |
| 2002/0013616 | A1 | 1/2002 | Carter et al. |
| 2002/0016623 | A1 | 2/2002 | Kula et al. |
| 2002/0019660 | A1 | 2/2002 | Gianotti et al. |
| 2002/0022876 | A1 | 2/2002 | Richter et al. |
| 2002/0042648 | A1 | 4/2002 | Schaldach et al. |
| 2002/0045933 | A1 | 4/2002 | Jang |
| 2002/0049490 | A1 | 4/2002 | Pollock et al. |
| 2002/0058990 | A1 | 5/2002 | Jang |
| 2002/0062149 | A1 | 5/2002 | Jang |
| 2002/0065549 | A1 | 5/2002 | White et al. |
| 2002/0095208 | A1 | 7/2002 | Gregorich et al. |
| 2002/0103529 | A1 | 8/2002 | Pinchasik et al. |
| 2002/0111669 | A1 | 8/2002 | Pazienza et al. |
| 2002/0123795 | A1 | 9/2002 | Jalisi |
| 2002/0161428 | A1 | 10/2002 | Oepen et al. |
| 2003/0139799 | A1 | 7/2003 | Ley |
| 2004/0073291 | A1 | 4/2004 | Brown et al. |

FOREIGN PATENT DOCUMENTS

| | | |
|---|---|---|
| DE | 10223399 | 12/2003 |
| EP | 0421729 | 10/1990 |
| EP | 0177330 | 6/1991 |
| EP | 0421729 | 1/1996 |
| EP | 0801934 | 6/2000 |
| EP | 1095632 | 10/2000 |
| EP | 0931520 | 5/2001 |
| EP | 1095632 | 5/2001 |
| EP | 1095633 | 5/2001 |
| EP | 1356789 | 10/2003 |
| EP | 1095633 | 12/2004 |
| WO | 9732543 | 8/1997 |
| WO | WO9732543 | 9/1997 |
| WO | WO9733534 | 9/1997 |
| WO | 9939660 | 8/1999 |
| WO | WO9939660 | 8/1999 |
| WO | 0006051 | 2/2000 |
| WO | WO0006051 | 2/2000 |
| WO | 0013611 | 3/2000 |
| WO | WO0013611 | 3/2000 |
| WO | 0035378 | 6/2000 |
| WO | WO0035378 | 6/2000 |
| WO | 0054704 | 9/2000 |
| WO | WO0054704 | 9/2000 |
| WO | 0101885 | 1/2001 |
| WO | WO0101885 | 1/2001 |
| WO | 0115632 | 3/2001 |
| WO | WO0115632 | 3/2001 |
| WO | 0126583 | 4/2001 |
| WO | WO 01/26583 A1 * | 4/2001 |
| WO | WO0126583 | 4/2001 |
| WO | 0137761 | 5/2001 |
| WO | 0189414 | 5/2001 |
| WO | WO0137761 | 5/2001 |
| WO | WO0189414 | 11/2001 |
| WO | 0200138 | 1/2002 |
| WO | 0205863 | 1/2002 |
| WO | WO0200138 | 1/2002 |
| WO | WO0205863 | 1/2002 |
| WO | 0215820 | 2/2002 |
| WO | WO0215820 | 2/2002 |
| WO | 0224111 | 3/2002 |
| WO | 0224112 | 3/2002 |
| WO | WO0224111 | 3/2002 |
| WO | WO0224112 | 3/2002 |
| WO | 0234162 | 5/2002 |
| WO | 0234163 | 5/2002 |
| WO | 0238080 | 5/2002 |

| | | | | | | |
|---|---|---|---|---|---|---|
| WO | WO0234162 | 5/2002 | | WO | 02080814 | 10/2002 |
| WO | WO0234163 | 5/2002 | | WO | WO02078570 | 10/2002 |
| WO | WO0238080 | 5/2002 | | WO | WO02080814 | 10/2002 |
| WO | 02051335 | 7/2002 | | WO | 02091951 | 11/2002 |
| WO | 02051462 | 7/2002 | | WO | WO02091951 | 11/2002 |
| WO | 02054986 | 7/2002 | | WO | 03002037 | 1/2003 |
| WO | 02056795 | 7/2002 | | WO | 03007842 | 1/2003 |
| WO | WO02051335 | 7/2002 | | WO | WO03002037 | 1/2003 |
| WO | WO02051462 | 7/2002 | | WO | WO03007842 | 1/2003 |
| WO | WO02054986 | 7/2002 | | WO | WO03047651 | 6/2003 |
| WO | WO02056795 | 7/2002 | | WO | WO03094798 | 11/2003 |
| WO | 02068037 | 9/2002 | | WO | WO2004064911 | 8/2004 |
| WO | WO02068037 | 9/2002 | | | | |
| WO | 02078570 | 10/2002 | | * cited by examiner | | |

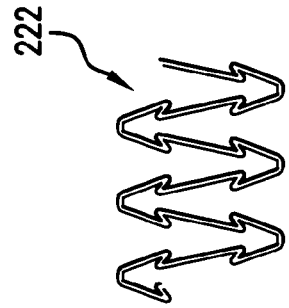
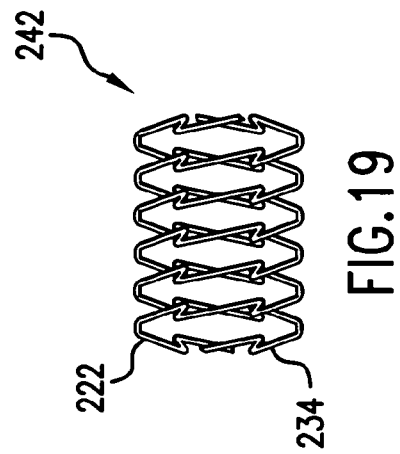
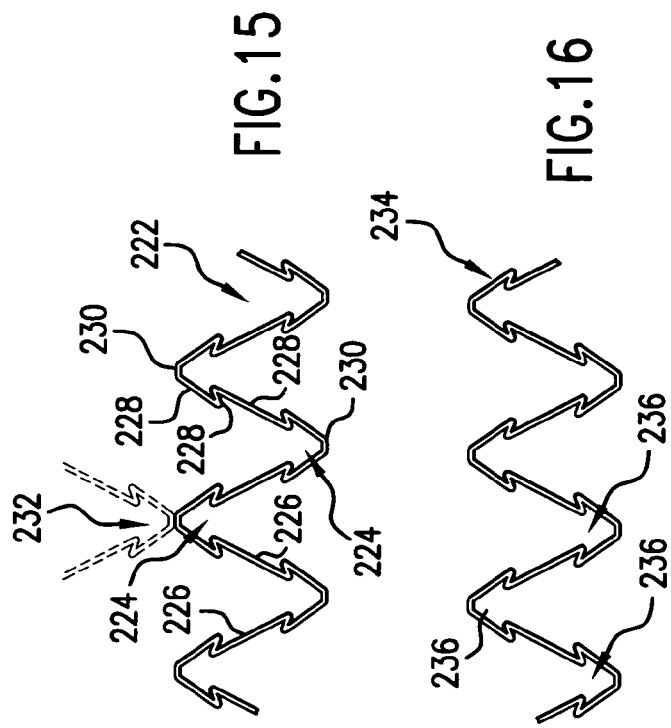
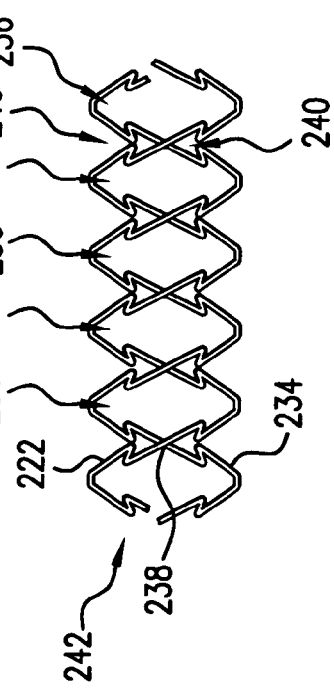

ENDOPROSTHESIS FOR CONTROLLED CONTRACTION AND EXPANSION

CROSS-REFERENCE TO RELATED APPLICATIONS

This application claims the benefit of Provisional Patent Application No. 60/378,278, filed May 6, 2002; No. 60/378,279, filed May 6, 2002; No. 60/378,345, filed May 8, 2002; and No. 60/379,310, filed May 8, 2002; the content of each application is expressly incorporated herein by reference thereto.

FIELD OF THE INVENTION

The present invention relates to an endoprosthesis having delivery and deployed configurations for implantation into a vessel. More particularly, the invention relates to a stent with improved contraction and expansion characteristics.

BACKGROUND OF THE INVENTION

Stents, grafts and a variety of other endoprostheses are well known and used in interventional procedures, such as for treating aneurysms, for lining or repairing vessel walls, for filtering or controlling fluid flow, and for expanding or scaffolding occluded or collapsed vessels. Such endoprostheses can be delivered and used in virtually any accessible body lumen of a human or animal, and can be deployed by any of a variety of recognized means. One recognized indication of endoprostheses, such as stents, is for the treatment of atherosclerotic stenosis in blood vessels. For example, after a patient undergoes a percutaneous transluminal coronary angioplasty or similar interventional procedure, an endoprosthesis, such as a stent, is often deployed at the treatment site to improve the results of the medical procedure and to reduce the likelihood of restenosis. The endoprosthesis is configured to scaffold or support the treated blood vessel; if desired, the endoprosthesis can also be loaded with a beneficial drug so as to act as a drug delivery platform to reduce restenosis or the like.

The endoprosthesis is typically delivered by a catheter delivery system to a desired location or deployment site inside a body lumen of a vessel or other tubular organ. To facilitate such delivery, the endoprosthesis must capable of having a particularly small cross profile to access deployment sites within small diameter vessels. Additionally, the intended deployment site is often difficult to access by a physician and involves traversing the delivery system through the tortuous pathway of the anatomy. It therefore is desirable to provide the endoprosthesis with a sufficient degree of longitudinal flexibility during delivery to allow advancement through the anatomy to the deployed site.

Once deployed, the endoprosthesis should be capable of satisfying a variety of performance characteristics. The endoprosthesis should have sufficient rigidity or outer bias when deployed to perform its intended function, such opening a lumen or supporting a vessel wall. Similarly, the endoprosthesis should have suitable flexibility along its length when deployed so as not to kink or straighten when deployed in a curved vessel. It also may be desirable to vary the rigidity or flexibility of the endoprosthesis along its length, depending upon the intended use. Additionally, it may be desirable for the endoprosthesis to provide substantially uniform or otherwise controlled coverage, e.g., as determined by the ratio of the outer surface of the endoprosthesis to the total surface of the vessel wall along a given length. For example, increased coverage may be desired for increased scaffolding, whereas decreased coverage may be desired for side access to branch vessels. Control of the cross profile and length of the endoprosthesis upon deployment also is desirable, at least for certain indications.

Particularly, tradeoffs are traditionally required between device performance during the interventional procedure, in which an endoprosthesis is placed in a vessel, and long term device performance. Excellent placement performance (deliverability, ease of access, stent retention, etc.) favors a stent design that is highly flexible and that has a low profile. Long-term device performance (e.g., coverage, scaffolding, low restenosis) often requires a stent with significant rigidity or outer bias to support the vessel. High scaffolding stents employ a relatively large amount of metal, and this metal can restrict how tightly the stent can be crimped, thus limiting its profile, retention on an expansion balloon, and deliverability performance. The following formula illustrates the relationship between inner diameter (ID) and strut width and number (i.e., scaffolding) in a particular cross-section of a traditional crimped stent, where n is the number of struts and w is the width of each strut:

$$ID = \frac{\text{circumference}}{\pi} = \frac{nw}{\pi}$$

The deliverability of a stent device can be also limited by the amount of material at the distal end of the delivery catheter. The force exerted by stent geometry generally corresponds to the amount of strain in the material, which increases as the stent geometry is deformed from the set state. A traditional stent that is set, such as by heat, in the expanded state exerts the greatest force when it is the most crimped, and a typical stent that is heat set in the crimped state exerts the greatest force when it is the most expanded. The material of typical stents either keeps the stent crimped on the delivery system during delivery or expands the stent at the site of treatment. Traditional stents can only accomplish one of these two tasks and require significant additional material on the delivery system to accomplish the other. Balloon expandable stents, typically made of stainless steel, have mechanical properties allowing them to be easily and securely crimped on a delivery catheter. However, they require a relatively bulky balloon to expand them into the vessel wall. On the other hand, self-expanding stents made of NiTi alloy or other superelastic materials readily deploy themselves at the site of treatment but use a relatively bulky sheath to keep them constrained on the delivery system during delivery. Both traditional catheter balloons and stent sheaths tend to add significant profile and stiffness to the distal end of the implantation device.

Significant research effort has been devoted to the task of developing higher performance balloons (lower profile, more flexible) to minimize their impact on the delivery of the system. Similarly much work has focused on minimizing the impact of a constraining sheath for self-expanding stents. The use of such low profile, highly flexible delivery system could be furthered by the development of a stent or similar endoprosthesis that requires less force to maintain mounted on and deployed from the delivery system.

Numerous designs and constructions of various endoprosthesis embodiments have been developed to address one or more of the performance characteristics summarized above. For example, a variety of stent designs are disclosed in the following patents: U.S. Pat. No. 4,580,568 to Gianturco; U.S.

Pat. No. 5,102,417 to Palmaz; U.S. Pat. No. 5,104,404 to Wolff; U.S. Pat. No. 5,133,732 to Wiktor; U.S. Pat. No. 5,292,331 to Boneau; U.S. Pat. No. 5,514,154 to Lau et al.; U.S. Pat. No. 5,569,295 to Lam; U.S. Pat. No. 5,707,386 to Schnepp-Pesch et al.; U.S. Pat. No. 5,733,303 to Israel et al.; U.S. Pat. No. 5,755,771 to Penn et al.; U.S. Pat. No. 5,776,161 to Globerman; U.S. Pat. No. 5,895,406 to Gray et al.; U.S. Pat. No. 6,033,434 to Borghi; U.S. Pat. No. 6,099,561 to Alt; U.S. Pat. No. 6,106,548 to Roubin et al.; U.S. Pat. No. 6,113,627 to Jang; U.S. Pat. No. 6,132,460 to Thompson; and U.S. Pat. No. 6,331,189 to Wolinsky; each of which is incorporated herein by reference.

Although the various designs for endoprostheses that have been developed to date may address one or more of the desired performance characteristics, there remains need for a more versatile design for an endoprosthesis that allows improvement of one or more performance characteristics without sacrificing the remaining characteristics.

SUMMARY OF THE INVENTION

The present invention provides an endoprosthesis with improved control over its contraction and expansion. A preferred embodiment of the endoprosthesis has a plurality of annular elements, each of which is connected to an adjacent annular element at least one connection location. Each annular element includes an interconnected series of strut members. Selected strut members are each connected to an adjacent strut member at a longitudinal apex and extend to a strut end portion located on a longitudinally opposite side of the annular element from the apex. At least one of the strut members includes a first end portion and a first end of the strut member located at the strut end portion. At least this strut member also has an intermediate portion hingedly connected to the first end portion, and a second end portion hingedly connected to an intermediate portion and extending to the apex. The endoprosthesis preferably has a delivery diameter when in a delivery condition and a deployed diameter when in a deployed condition.

A circumferential member is preferably connected between corresponding ends of at least one pair of adjacent strut members to form a contoured arrowhead shape. This shape can be defined at a selected apex. At least one pair of adjacent strut members are preferably hingedly connected together to form the arrowhead shape, which can define a five-point hinge configuration. This adjacent pair of strut members of the arrowhead shape can extend substantially equally in opposite circumferential directions when the endoprosthesis is in the deployed condition. Also, the connection location at which the annular elements are connected can be the arrowhead of at least one of the adjacent annular elements.

The intermediate portion of the strut members in the preferred embodiment is disposed at an angle of less than about 90° to the first end portion, and preferably also to the second end portion. One or more of the arrowheads preferably defines a tip at the apex, with the intermediate portion disposed at an angle of about 90° or less to the longitudinal axis of the endoprosthesis in the deployed condition.

In the preferred embodiment, the first and second end portions of at least one strut member extend in a circumferential direction, and the intermediate portion thereof extends in an opposite circumferential direction to the final lightning bolt shape. The portions of the strut can thus be hingedly connected to each other at elbows. Also, each portion of the strut can be a substantially straight member, and in the delivery condition, the strut members can be substantially aligned within the longitudinal axis of the endoprosthesis.

A preferred endoprosthesis has strut members interconnected to form a repeated pattern of interconnected cells. Each cell has at least two arrowhead portions extending longitudinally and directed in opposite directions. Each arrowhead portion is connected with an arrowhead portion of an adjacent cell, and the cells are connected in a generally tubular shape, which can be in the delivery condition for facilitating delivery of the endoprosthesis to the deployment site, or the deployed condition for deployment in a vessel at the deployment site. Preferably, the arrowhead portions are configured to compensate for foreshortening of the endoprosthesis during expansion from the delivery to the deployed condition.

In one embodiment of the invention, the endoprosthesis could have a cell-defining structure that is radially expandable from a first diameter to a second diameter. The cell-defining structure defines at least one cell and includes a first set of strut members defining a base cell section and a second set of strut members defining an upper cell section that has a generally trapezoidal shape when the cell-defining structure is in the second diameter. The upper cell section preferably has generally parallel opposing sides, one of which is generally aligned with a first side of the base cell section. The base cell section can have a quadrilateral shape when the second cell-defining structure is in the second diameter, and this quadrilateral shape is preferably a parallelogram. Additionally, the base cell section can have a major and a minor axis, the major axis being oriented generally longitudinally with respect to the cell-defining structure.

The cell-defining structure can further include a third set of strut portions defining a lower cell section that has a generally trapezoidal shape when the cell-defining structure has the second diameter. The lower cell section preferably has generally parallel opposing sides, one of which is generally aligned with the second set of the base cell section that is opposite the first side thereof.

The cell-defining structure preferably defines a plurality of cells, with each cell having a base cell section, an upper cell section, and a lower cell section. Each of the upper and lower sections are preferably disposed at opposite sides of their respective base cell sections, and each cell from the plurality of cells can be connected to a circumferentially adjacent cell by a strut member that extends between adjacent upper and lower cell sections. The strut members can be common strut members of two longitudinally adjacent base cell sections.

A plurality of circumferentially adjacent cells can be arranged to provide at least two adjacent annular elements. These adjacent annular elements can have common strut portions defining adjacent upper and lower cell sections. When the cell-defining structure has a first diameter, one of the strut members of the second set of strut members is preferably folded towards one of the strut members of the first set of strut members, and one of the strut members of the third set of strut members can be folded towards one of the strut members of the first set of strut members.

An embodiment of the endoprosthesis has a series of interconnected strut members with a repeating group of a first generally longitudinal strut member, a first angled strut member contoured to have a nesting feature, and a second longitudinal strut member. The nesting feature is preferably configured for nestingly receiving at least one longitudinal strut member therein when the endoprosthesis body has the first diameter. The first and second ones of the annular elements preferably share a common second angled strut member. Also, the first and second annular elements can be connected by a connector member. The strut member that is nestingly received in the nesting feature can be a strut member of the first or second sets. In one embodiment of the endoprosthesis, a generally tubular scaffolding body thereof has an outer component that includes a first set of interconnected strut members and an inner component that includes a second set of interconnected strut members. The first set of interconnected strut members overlaps the second set of interconnected strut members, such as in a radial direction, to define a cooperating cell pattern. The inner and outer components preferably comprise inner and outer tubes, which can be substantially coaxial. The first and second sets of interconnected strut members can be abutting when the tubular scaffolding body is in the expanded, or delivery, state. Also, each of the inner and outer components can independently comprise an integral tubular structure.

The tubular scaffolding body of an endoprosthesis according to the invention can be configured with a first bias when in a first range of diameter between compressed and expanded diameters, and a second bias when in a second range of diameter between the first range and the expanded diameter. The second bias is expansive and has a greater expansive magnitude than the first bias. In one embodiment, the body naturally tends to contract when the body is smaller than a predetermined diameter and then naturally expand when the body is larger than a predetermined diameter.

Preferably, the body includes a contractile portion that is biased to contract the body, and also an expansive portion that is biased to expand the body. The contractile portion is preferably disposed within the expansive portion. Also, the contractile and expansive portions can be disposed in longitudinally adjacent annular elements of the body. With this layout, a plurality of longitudinal spines can couple the plurality of adjacent rings, and at least one of the longitudinal spines can extend across at least three adjacent annular rings, preferably providing either contractive or expansive forces at the ends thereof, with opposite forces in the middle thereof.

One of the contractile and expansive portions can comprise an outer tubular structure with the other comprising an inner tubular structure received coaxially within the outer tubular structure. Preferably the contractile portion comprises the outer tubular structure, and the expansive portion comprises the inner tubular structure.

Additionally, the contractile portion can have a geometry for decreasing the leverage of its bias when the body is expanded, and the expansive portion can have a geometry for increasing the leverage of its bias when the body is expanded. One embodiment of the endoprosthesis has a generally tubular scaffolding body that includes a first portion tending to contract and a second portion tending to expand when the body is at a predetermined diameter.

Another endoprosthesis embodiment has a tubular scaffolding body that is biased for expanding towards an expanded diameter from a contracted diameter. The body is configured such that the bias increases as the diameter approaches the expanded diameter from the contracted diameter. The bias can increase at any selected part of the expansion, either as it begins to expand from the contracted diameter, as it finalizes its expansion to the expanded diameter, or somewhere in between. This is preferably achieved by providing a contractile portion with a first geometry for decreasing the leverage of the bias thereof when the body is expanded and an expansive portion with a geometry for increasing the leverage thereof when the body is expanded.

A preferred method of manufacturing the endoprosthesis comprises setting a contractile portion of the endoprosthesis body to bias the body to contract the diameter and setting an expansive portion of the endoprosthesis body to bias the body to expand the diameter that is larger than the contracted diameter. Preferably, each of the contractile and expansive portions are formed as a tubular structure, one of which is placed within and coupled with the other.

In a preferred method of expanding an endoprosthesis, the endoprosthesis has both a contractile portion and an expansive portion positioned on a balloon of an endoprosthesis delivery catheter. The balloon is inflated to an intermediate endoprosthesis diameter that is less than the fully expanded diameter thereof. In this manner, the balloon causes the endoprosthesis to expand only to the intermediate endoprosthesis diameter, and the expansive section of the endoprosthesis expands the endoprosthesis to its fully expanded diameter. Preferably, the balloon has a maximum inflated diameter that is at most equal to the intermediate endoprosthesis diameter. The balloon is preferably inflated to a pressure that will selectively cause it to only inflate to the intermediate endoprosthesis diameter.

BRIEF DESCRIPTION OF THE DRAWINGS

FIGS. 15 and 16 are planar views of portions of inner and outer stent components, respectively, of a multilayer stent embodiment according to the invention in an expanded state;

FIG. 17 is a planar view of a portion of the multilayer stent with the inner and outer components of FIGS. 15 and 16 combined in the expanded state;

FIG. 18 is a planar view of the inner component of FIG. 15 in a contracted state;

FIG. 19 is a planar view of the combined portion of FIG. 17 in a contracted state;

DETAILED DESCRIPTION OF THE PREFERRED EMBODIMENTS

Figure 1:
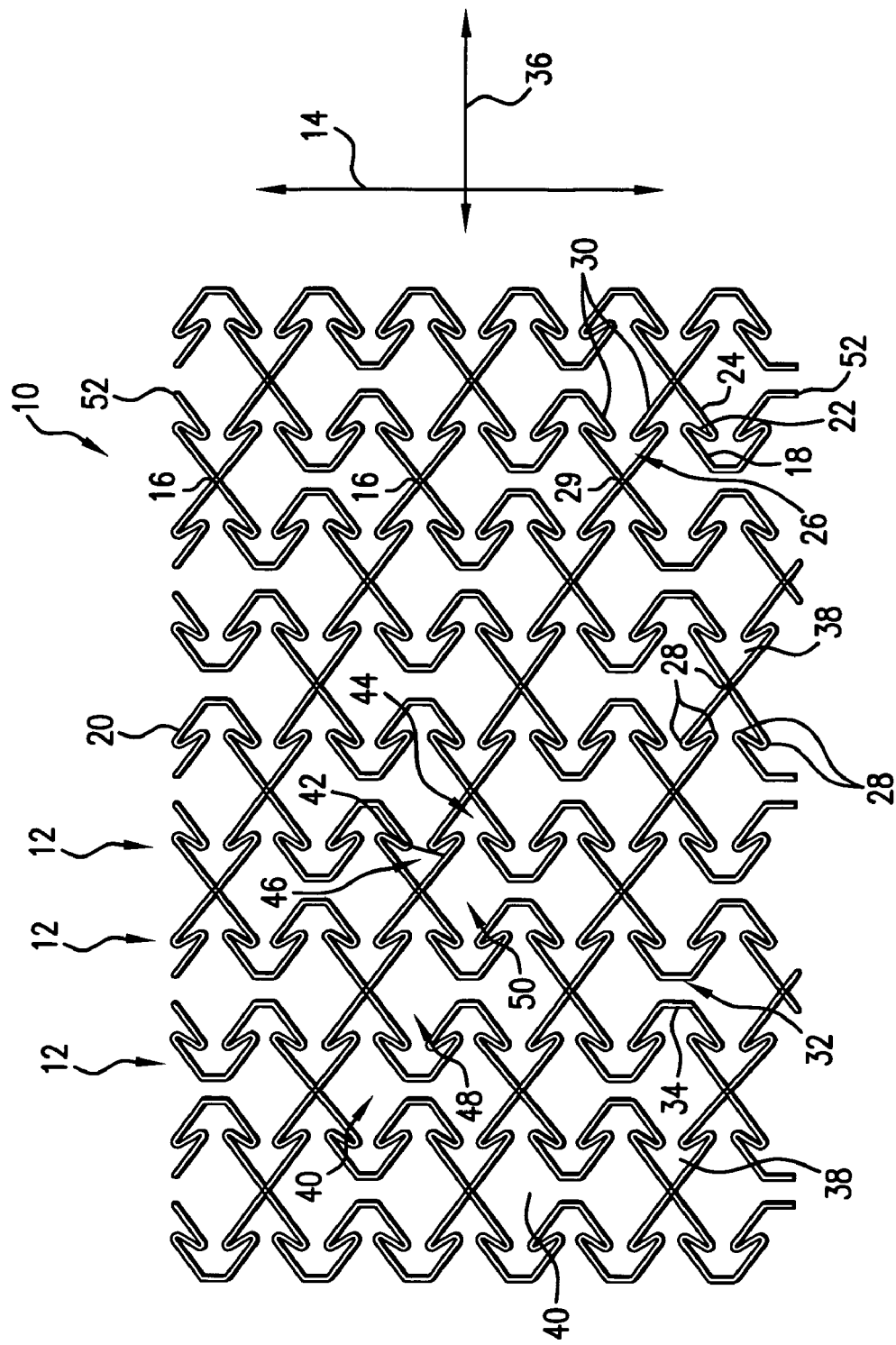
FIG. 1 is a planar view of an embodiment of a stent cell-pattern constructed according to the invention in a deployed configuration.

In accordance with the present invention, an endoprosthesis is provided for delivery within a body lumen of a human or animal. The endoprosthesis can include, but is not limited to, stents, stent grafts, valves, occlusive devices and aneurysm treatment devices or the like. The endoprosthesis of the present invention can be configured for a variety of intraluminal applications, including vascular, coronary, biliary, esophageal, gastrointestinal, urological or the like. The present invention provides improved control to the contraction, expansion, and the contracted and expanded states of the endoprosthesis.

Generally, the endoprosthesis of the present invention includes a first set of interconnected strut members defining a first annular element, and a second set of interconnected strut members defining a second annular element. The endoprosthesis can include only one annular element if suitable, or additional annular elements defined by interconnected strut members as desired or needed. Each annular element defines a structure extending circumferentially about a longitudinal axis. The cross profile of each annular element preferably is at least arcuate, and more preferably either circular or spiral, although alternative cross profiles, such as rectilinear or the like, can be used if desired.

The first annular element is aligned longitudinally adjacent to the second annular element along the longitudinal axis, and connected to each other at least one connection location. Preferably, the first and second annular elements generally define a tubular structure. For example, each annular element can define a continuous closed ring such that the longitudinally-aligned annular elements form a closed tubular structure having a central longitudinal axis. Alternatively, each annular element can define an open ring such that a rolled sheet or open tubular type structure is defined by the annular elements.

Each strut member of the annular elements includes a first end and a second end. The strut members of each annular element are disposed circumferentially adjacent to each other, and interconnected so as to define an expandable structure. For example, and with reference to the closed tubular structure above, circumferentially-adjacent strut members of each annular element can be interconnected, either directly or indirectly, in an end-to-end format to define a continuous ring having a generally circular cross profile. By altering the angle or distance defined between circumferentially-adjacent strut members, as well as by opening or unfolding the portions of each stent as described further below, the tubular structure can be radially expanded between a delivery configuration and a deployed configuration. As discussed in detail below, the expandable structure can be expanded by the application of an external force, such as by a balloon, or by a change in delivery conditions, such as an increase in temperature or the removal of a restraint, so as to allow the structure to self expand.

In accordance with one aspect of the invention, an endoprosthesis is provided having a plurality of annular elements that are connected to adjacent annular elements at least one connection location. Each annular element includes an interconnected series of strut members, each connected to an adjacent strut member at a longitudinal apex and extending to a strut end portion at a location on the longitudinally opposite side of the annular element from the apex. At least one of the strut members includes a first end portion, an intermediate portion, and a second end portion. The first end portion is located at the strut end portion. The intermediate portion is hingedly connected to the first end portion. The second end portion is hingedly connected to the intermediate portion and extends to the apex. The endoprosthesis has a delivery diameter when in a delivery condition and a deployed diameter when in a deployed condition.

With reference to FIG. 1, for purpose of illustration and not limitation, a representative embodiment of an endoprosthesis, which in this embodiment is a stent 10 of the present invention, is depicted in a planar format for clarity. As shown in FIG. 1, the stent 10 includes a plurality of annular elements 12 arranged generally circumferentially and disposed and preferably aligned adjacent to each other along a longitudinal axis 36. Although only one annular element need be provided, it is preferable that the stent 10 include a plurality of annular elements 12, defined herein at least by first and second annular elements 12. The annular elements 12 are preferably longitudinally displaced from or adjacent to each other and are connected to an adjacent annular element 12 at least one connection location 16.

The annular elements 12 include an interconnected series of strut members 20. Each strut member 20 of the embodiment shown in FIG. 1 has an end portion 18 at a first end of the strut member 20, an intermediate portion 22 hingedly connected to the first end portion, and a second portion 24 hingedly connected to intermediate portion 22.

Preferably, at least one pair of adjacent strut members 20 are hingedly connected together to form an arrowhead shape 26, defined by the first end portion 18, intermediate portion 22, and second end portion 24. This configuration generally can be construed as a five point hinge, with hinge points 28 between the portions.

The arrowhead portions 26 preferably include two circumferential sides 30 that are preferably mirror images of each other, but in other embodiments may differ from each other. Each circumferential side 30 comprises a first end portion 18, an intermediate portion 22, and a second end portion 24. Preferably attached end to end, these portions 18,22,24 extend along a lightning-bolt shaped path that doubles back upon itself, with hinges or elbows that generally reverse the direction of the path between portions 18,22,24, so as to collapse in a folding or accordion manner. All of the portions 18,22,28 are preferably oriented at an angle to both the longitudinal and circumferential axes 36,14 when deployed. In this embodiment, the portions of the strut members 20 are substantially straight, but can be curved in other embodiments. For example, the first and/or second end portions can be contoured to allow the intermediate portion to nest therein when in the delivery state. Also, the hinges between the arrowhead portions are preferably sharp angles, although can be rounded to remove stress concentration if desired. Each side 30 of the arrowhead shape 26 preferably extends substantially equally in opposite circumferential directions, but in alternative embodiments, may extend to each side by a different amount.

As shown in FIG. 1, selected ends can be connected directly together to define an apex 29 at the tip of the arrowhead shape 26. In the embodiment of FIG. 1, each sharp apex 29 is connected to an apex 29 of an opposing arrowhead shape 26 at a connection location 16. In an alternative embodiment, however, the arrowhead shapes 26 may protrude into each other, or a separate longitudinal connector can be provided therebetween.

As further embodied herein, some of the arrowhead shapes 32 are longitudinally free from connection to adjacent annular elements 12. These longitudinally free arrowhead shapes 32 preferably have a shorter longitudinal extent than the sharp arrowheads that are connected to adjacent annular members 12. The opposing second end members 24 on each side of the free arrowheads 32 are connected by a circumferential member 34, which is disposed in substantial alignment with the circumferential direction 14 to form a blunt arrowhead shape as embodied herein. Alternatively, a V-shaped or otherwise contoured member can be provided. The blunt or flat arrowhead shapes can provide a height or circumferential direction of the flat apex at the end of a longitudinally free arrowhead that is equivalent or slightly less than the height of the remaining folding members of the annular elements, including the struts and strut portions, in the delivery condition. This aids in maximizing packing density.

In alternative embodiments, some or all connection locations can be disposed on the circumferential members 34. For example, a straight or curved connector can extend longitudinally between the circumferential members 34 to connect adjacent annular elements. In these embodiments, a large range of phase differences can be selected between adjacent annular elements 12, as the circumferential elements 34 provide a wide base for the connection locations 16, providing versatility in the design of the pattern.

The annular elements 12 are preferably similar to each other in a particular stent pattern. In other embodiments, the layout and configuration of the annular elements 12 can be varied for desired characteristics such as varied rigidity or flexibility. Additionally, the pattern formed by the strut members 20 of annular elements 20 can be in or out of phase with those of adjacent annular elements 12. In FIG. 1, the patterns of adjacent annular members 12 are 180° out of phase, which can be seen as the apices 29 and circumferential members 34 of adjacent annular elements 12 are directly opposed and substantially in alignment with and facing towards and away from each other. Embodiments with annular members 12 that are in phase have circumferentially aligned arrowheads all facing in the same longitudinal direction. The adjacent annular elements 12 that are connected with adjacent annular elements 12 are preferably positioned sufficiently out of phase so that the connection locations 16 are disposed at the arrowheads 26 of the adjacent annular elements 12, so that the arrowheads themselves are directly connected.

In the preferred embodiment, each annular member 12 defines a series of arrowheads 26 alternating in opposite longitudinal directions 36. Preferably, one or more free arrowheads 32 are disposed circumferentially adjacent to connected arrowheads 38 on adjacent annular elements or a selected side of each annular member 12 so that connected arrowheads 38 are not immediately circumferentially adjacent to each other in the preferred embodiment. The number of free arrowheads between connection locations can be varied in other embodiments.

In the preferred arrowhead shapes 26, the intermediate portions 22 are disposed at an angle of about 90° or less to the first end portion 18 and to the second end 24 portion when deployed. Also, the intermediate portions 22 are disposed at an angle of about 90° or less to the longitudinal axis when deployed, as measured on a longitudinal side of the intermediate portion 22 opposite from the tip of the arrowhead 26, Preferably, the circumferential width of the base of the arrowheads 26, at the end of the first end portions 18, opposite from the tip of the arrowheads 26, is wider than the midsection of the arrowheads 26, at the circumferentially widest portion of the intermediate portions 22.

Figure 2:
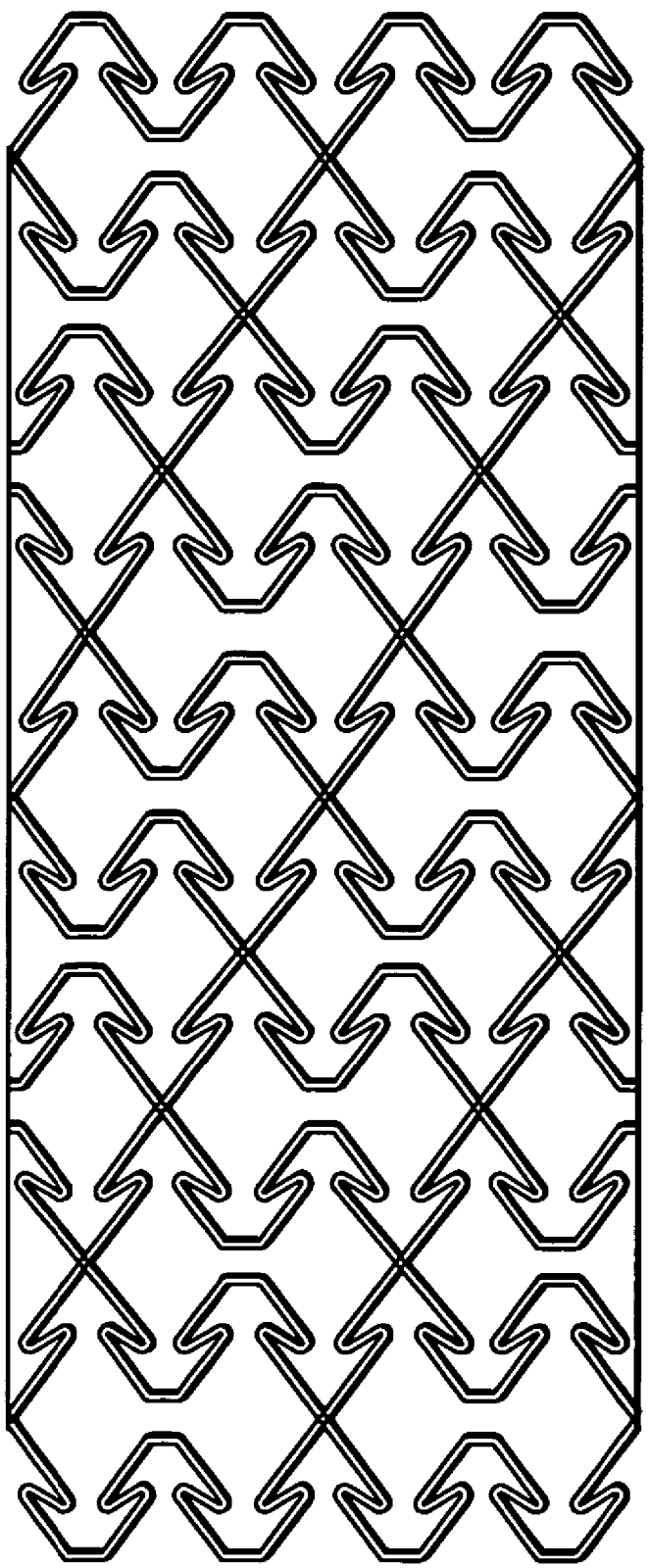
FIG. 2 is a side view of a stent having the cell-pattern of FIG. 1 in the deployed configuration.

The pattern 10 of the preferred embodiment is configured such that each portion of the strut members 20 is substantially aligned with the longitudinal axis of the stent when in the delivery configuration. In addition, the plurality of strut members 20 are interconnected to form a cell pattern that includes the arrowhead portions 26. Along the circumferential length of the annular elements 12 that define the cell patterns 40 are arrowheads 26 that point in opposite longitudinal directions and which preferably share common strut members 20. For instance, as shown in FIG. 1, first end portion 42 of arrowhead 44 is the second end portion of arrowhead 46. Similarly, the arrowheads 26 of the cells share the same boundaries and strut members 20 with adjacent cells in the preferred embodiment, such as cells 48 and 50. As shown in FIG. 2, the cells are connected in a generally cylindrical shape to define the cylindrical stent.

Figure 3:
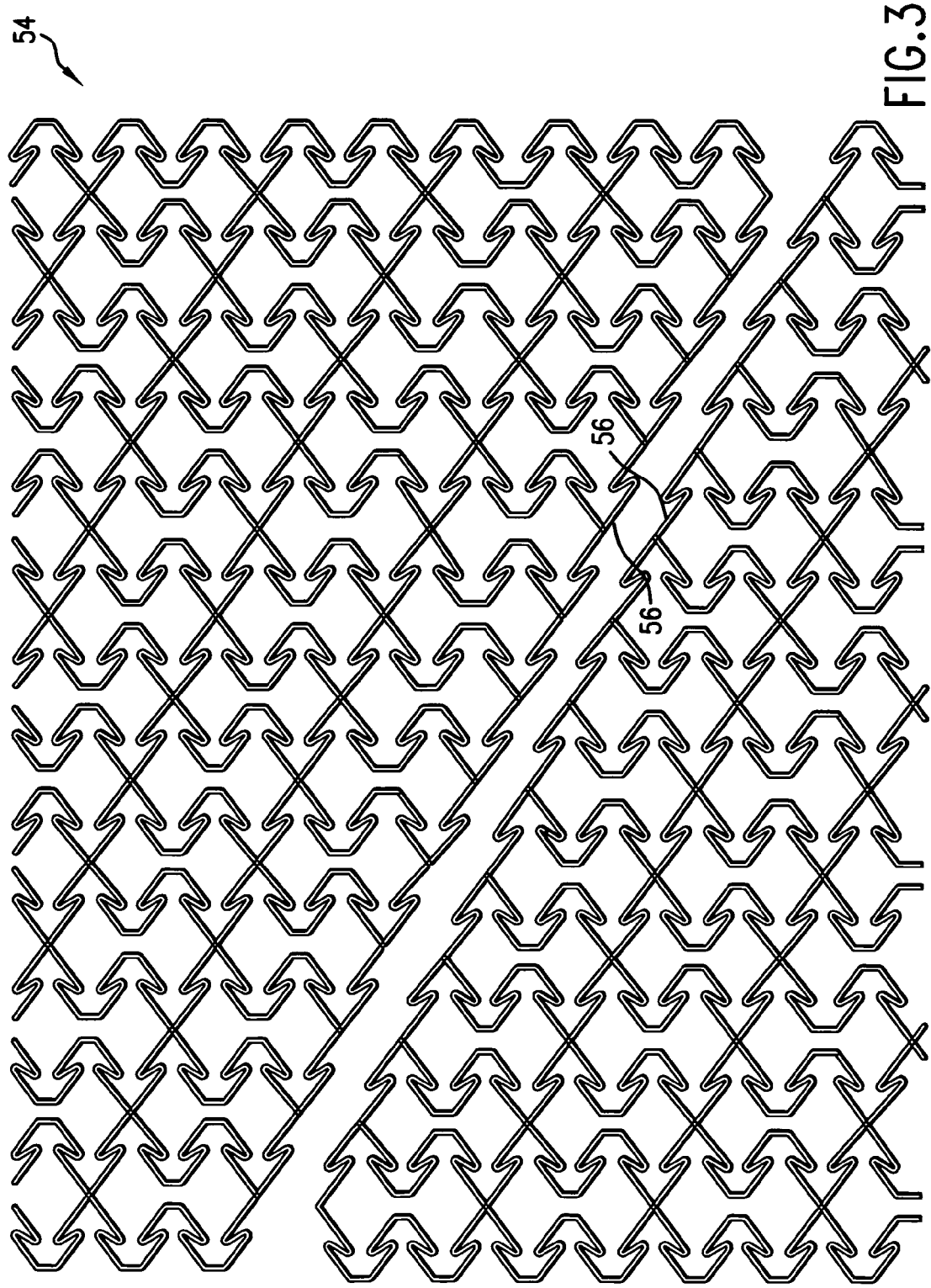
FIG. 3 is a planar view of another embodiment of a stent pattern similar to FIG. 1, but for a coiled-sheet stent.

The preferred stent is substantially cylindrical, and the circumferential edges of the stent 10 are preferably continuous with each other. In an alternative embodiment, the stent is made of a coiled sheet, in which the lateral edges of the pattern are not affixed to each other and in which the annular elements 12 are open. The coiled sheet can be delivered in a small diameter, coiled state to the deployment site, with the opposing edges of the sheet preferably configured for engaging each other when the stent is expanded to the deployed position, to prevent collapse of the stent. For example, uneven lateral edges can be used on the opposite circumferential edges 56 to hook with each other to prevent collapse. FIG. 3 shows a coiled sheet embodiment 54, with saw tooth circumferential edges 56 to catch in interlocking engagement with opposing saw tooth circumferential edges 56 to prevent collapse of the sheet from the deployed position. In this manner, the coil sheet will both unravel and expand circumferentially when deployed.

The connection locations 16 and, if present, any connectors extending between connection locations 16 on longitudinally adjacent annular elements 12, are preferably circumferentially displaced with respect to each other to improve flexibility of the stent. Another embodiment has all of the connection locations 16 aligned if desired.

The arrowhead portions 26 are preferably configured and dimensioned relative to the strut members and the remainder of the stent pattern to compensate for longitudinal foreshortening upon stent expansion. This is preferably achieved by the position and angle of the intermediate portions 22 with respect to the longitudinal axis and other strut portions. The intermediate portions 22 open in an elongating direction relative to the foreshortening which occurs as each pair of adjacent strut members open relative to each other. The geometry of the arrowhead portion can be selected otherwise to provide a desired amount of lengthening or shortening upon expansion, depending on the stent application and is preferably selected to provide an even distribution of strain in expanding areas of the stent. The arrowhead portions also are provided to improve and control the flexibility of the stent, preferably without substantially degrading the coverage thereof or the scaffolding the stent provides. In some embodiments, the arrowhead portions are configured to produce a torque on the longitudinally free protrusions of the pattern to bias these longitudinally free portions back inward towards the general cylindrical shape of the stent when the stent is flexed along its longitudinal axis. This feature can be increased or decreased if desired to embed portions of the stent into an arterial wall or other tissue.

To achieve these characteristics, several aspects of the geometry can be varied. These aspects include the strut member length, width, thickness and cross section; the shape and amount of hinge points within the arrowhead portions; the phase difference between adjacent annular elements; the number of connection locations and the length of any connectors; the number of apices or free arrowheads between connections; and the shape of strut members and any connectors.

In accordance with another aspect of the invention, an endoprosthesis is provided having a cell-defining structure that is radially expandable from a first diameter to a second diameter. The structure has at least one cell, which includes a first and a second set of stent members. The first set defines a base cell section. The second set defines an upper cell section that has a generally trapezoidal shape when the cell-defining structure is in the second diameter, and preferably generally parallel opposing sides. One of the opposing sides is preferably generally aligned with a first side of the base cell section.

Figure 4:
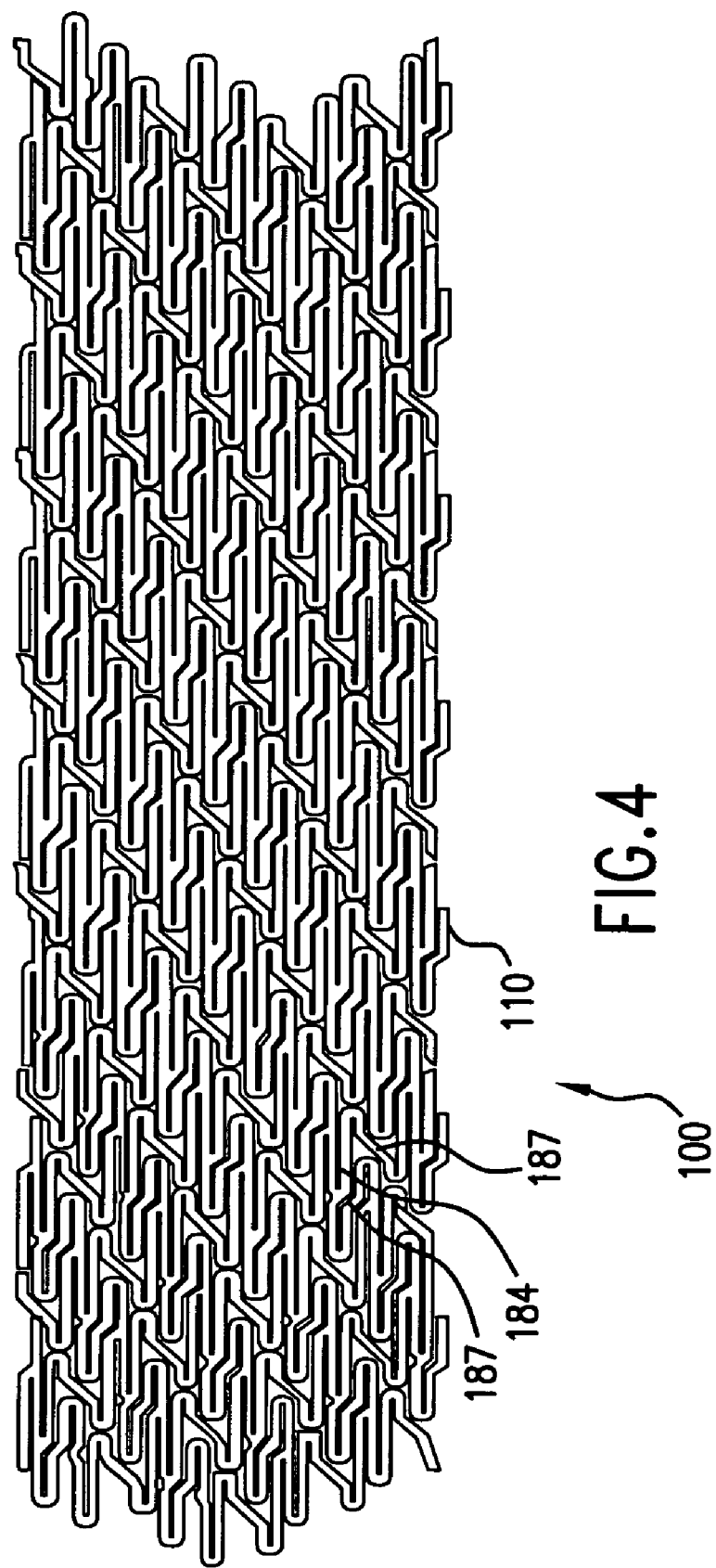
FIG. 4 is a planar side view of another embodiment of a stent cell-pattern in a delivery configuration in accordance with another aspect of the invention.
Figure 5:
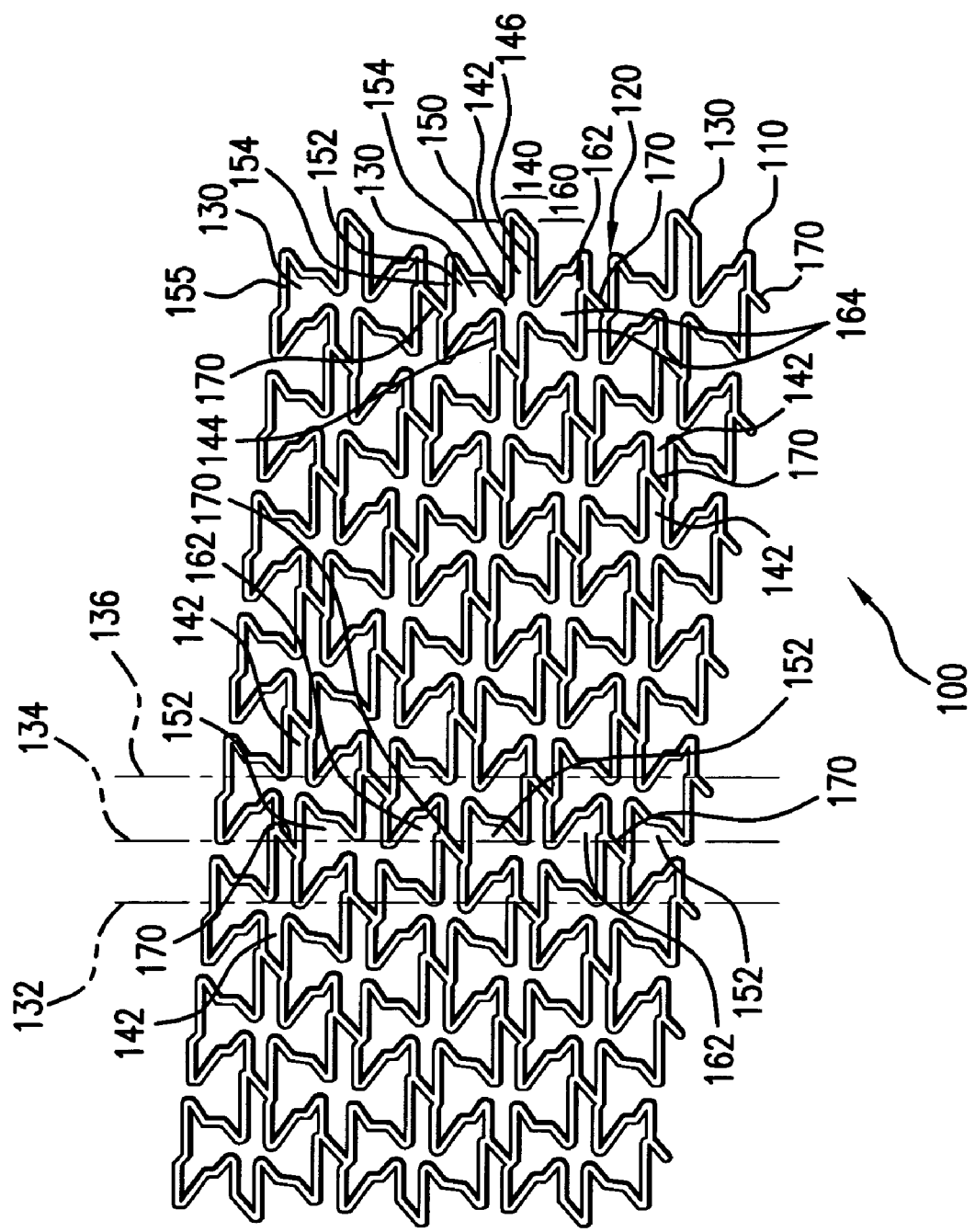
FIG. 5 is a planar side view thereof in a deployed configuration.

Referring to FIGS. 4 and 5, in one embodiment, a stent 100 includes a generally tubular stent body 110, which is radially expandable between a delivery configuration as shown in FIG. 4 and a deployed configuration as shown in FIG. 5. As shown in FIG. 4, the contracted configuration may be referred to as the "delivery" configuration or "crimped" configuration. The expanded configuration may be referred to as the "deployed" diameter.

Figure 7:
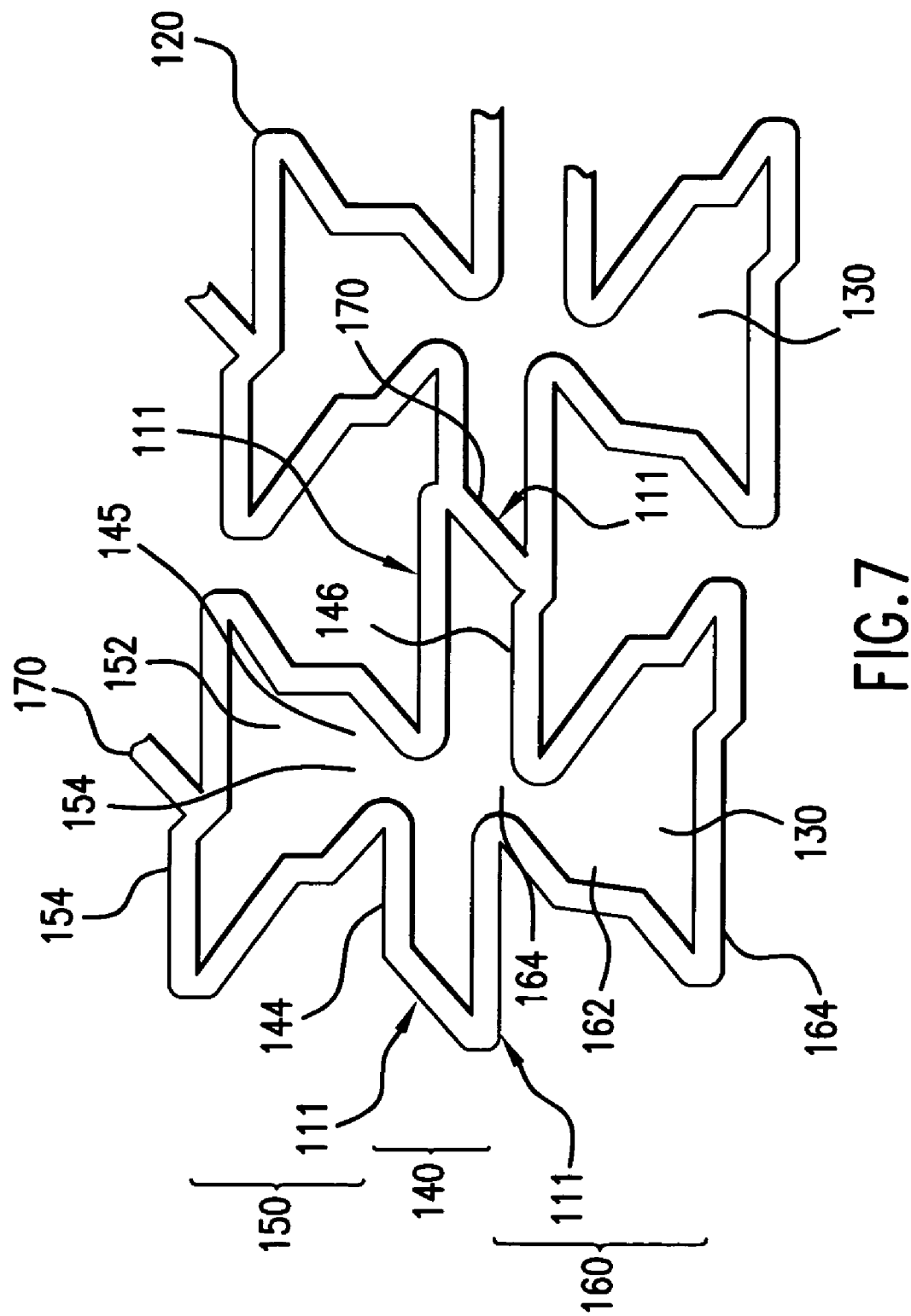
FIG. 7 is an enlarged, partial side view of the embodiment of FIG. 5, showing longitudinally adjacent cells.

Referring to FIGS. 5 and 7, the stent body 110 includes a cell-defining structure 120 defining at least one cell 130. The cell-defining structure 120 includes a first set of strut portions 140 defining a base cell section 142, and a second set of strut portions 150 defining an upper cell section 152. The upper cell section has a generally trapezoidal shape when the stent body has the expanded diameter, as shown in FIG. 5. The upper cell section 152 has generally parallel opposing sides 155, 154. The side 155 disposed longitudinally farthest from the base cell section includes a strut portion that forms a generally flat apex. The other of the generally parallel opposing sides 154 of the upper cell section is generally aligned with and defined by an opening 145 in a first side 144 of the base cell section 142. In the embodiment shown, the trapezoidal-shaped upper cell section 152 has an open side that corresponds to the opening 145 in the first side 144 of the base cell section 142. The opening 145 provides increased longitudinal flexibility to the stent.

The base cell section 142 has a generally quadrilateral shape when the stent body 110 has the expanded diameter. The quadrilateral shape is preferably a parallelogram having sides 111. The base cell section 142 may be considered to have a major axis and a minor axis. In the embodiment shown, the major axis is oriented generally longitudinally with respect to the stent body.

The cell-defining structure 120 may further include a third set of strut portions 160 defining a lower cell section 162 having a generally trapezoidal shape when the stent body has the expanded diameter. The lower cell section may have generally parallel opposing sides 164, similar to the upper cell section described above. One of the opposing sides 164 of the lower cell section 162 is preferably generally aligned with a second side 146 of the base cell section 142 that is opposite the first side 144 of the base cell section.

In the embodiment of FIG. 5, the cell-defining structure defines a plurality of cells 130, each cell having a base cell section, an upper cell section, and a lower cell section. Each of the upper and lower cell sections are oriented at circumferentially opposite sides of a respective base cell section, and each cell of the plurality of cells is connected to a circumferentially adjacent cell by a strut 170 extending between adjacent upper and lower cell sections. As shown, the strut 170 may be a common strut portion of two longitudinally adjacent base cell sections 142.

When a plurality of adjacent cells is provided to form a plurality of adjacent annular members, the cell-defining structure may define a plurality of cells arranged to define a uniform pattern throughout the stent body. The uniformity of the cell pattern may be provided in selected sections of the stent body, e.g. longitudinal sections may have differing uniform patterns, to provide selected characteristics of the stent, such as variable flexibility or scaffolding throughout the stent. Alternatively, the cell pattern can be configured such that a non-uniform pattern is provided.

The mechanism by which the stent body 110 is moved between the delivery configuration and the deployed configuration includes folding and nesting of the various strut portions making up the sections of the cells. For instance, as can be seen when comparing FIG. 4 and FIG. 5, one strut portion of the second set of strut portions is folded toward one strut portion of the first set of strut portions when the stent body has the delivery configuration. Also, when the stent body has the delivery configuration, one strut portion of the third set of strut portions is folded toward one strut portion of the first set of strut portions.

Another feature of the strut portions of the cell defining structure is that at least one strut portion of the first, second, or third sets of strut portions may be contoured to nest with an adjacent strut portion when the stent body has the contracted diameter so as to provide a nesting feature. For example, FIG. 5 shows a contour or detent in member 15 to receive member 120 when contracted to the delivery configuration as shown in FIG. 4. Similar contours are depicted in the angled side members of the upper and lower cell sections 152, 162.

The stent 100 preferably includes a plurality of circumferentially adjacent cells 130 that are arranged to provide at least two adjacent annular elements. A plurality of circumferentially adjacent cells 130 can be arranged to provide two or more longitudinally adjacent annular elements as identified in FIG. 5 for illustrative purposes. For example, a first annular element 180 is generally positioned between reference lines 132 and 134 and a second annular element 180 is positioned between reference lines 134 and 136. The lines 132, 134, 136 in FIG. 5 that indicate the adjacent annular elements 180 are shown extending along longitudinal edges of respective annular elements. The adjacent annular elements have common strut portions defining adjacent upper and lower cell sections as depicted more clearly in FIG. 6. The struts 170 extending between adjacent upper and lower cell sections 152 and 162 of the central annular element 134 include common strut portions of two longitudinally adjacent base sections 142 of the adjacent annular elements.

Figure 6:
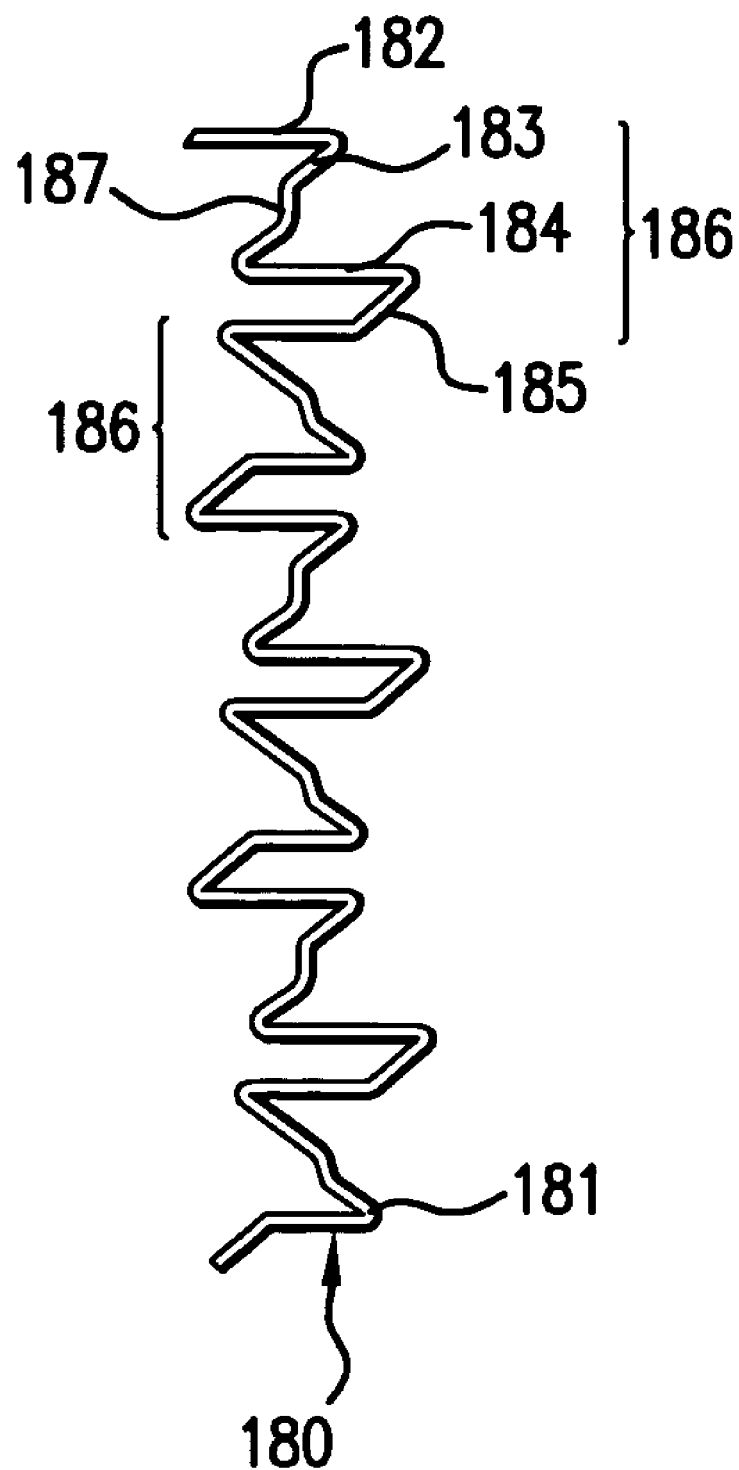
FIG. 6 is a planar view of an annular element thereof.
Figure 8:
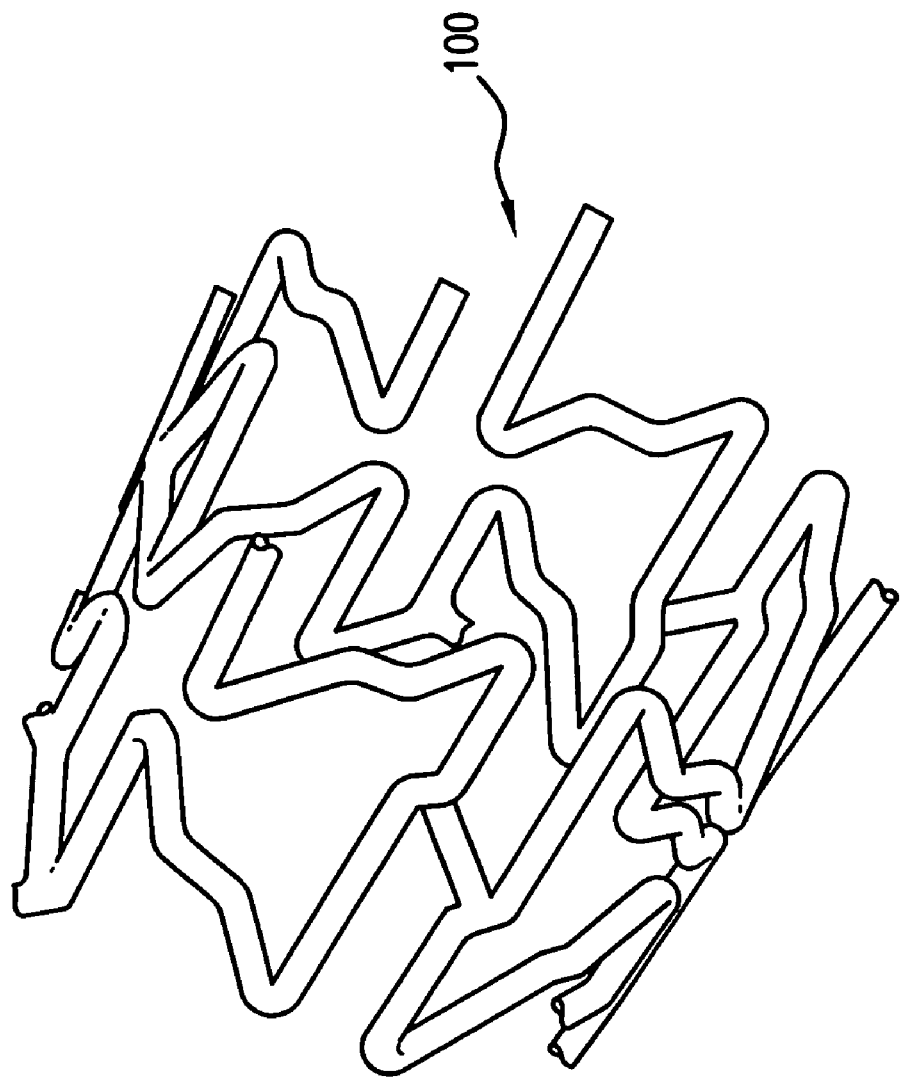
FIG. 8 is a partial perspective view of the embodiment of FIG. 5.
Figure 9:
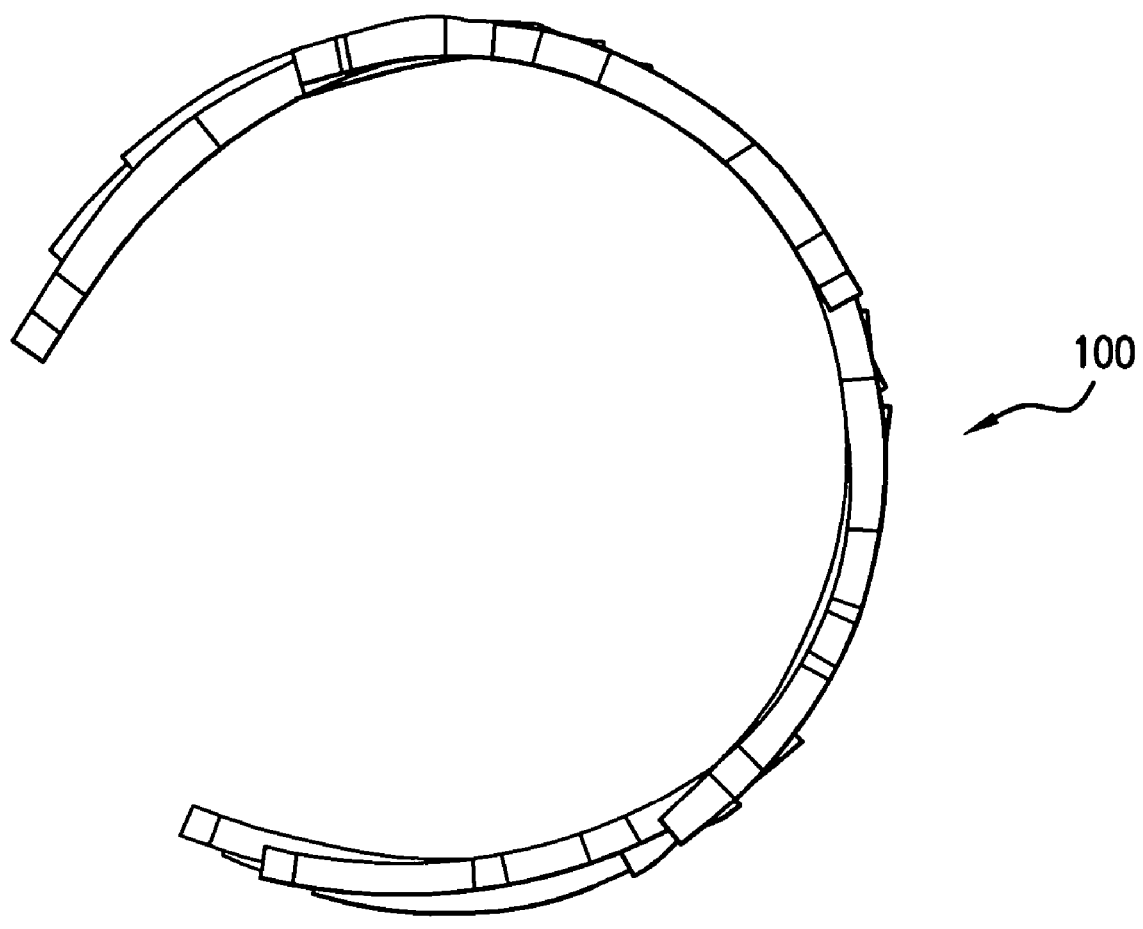
FIG. 9 is an end view of a modified embodiment of FIG. 5.

FIG. 6 shows a portion of the stent body that may be considered an annular element 180. The annular element 180 includes a first series of interconnected strut members 181. The first series of interconnected strut members includes a repeating group 186 of a first longitudinal strut 182, a first angled strut 183 having a nesting feature 187, a second longitudinal strut 184, and a second angled strut 185. Stents with this pattern are shown for the purpose of illustration in a closed-ring embodiment in FIG. 8, and in a coiled, open-tube embodiment in FIG. 9.

The stent body will further include a second annular element including a second series of interconnected strut members. The second series of interconnected strut members also will include a repeating group of a first longitudinal strut, a first angled strut having a nesting feature, a second longitudinal strut, and a second angled strut. In one embodiment, the first and second annular elements share at least one common second angled strut. In another embodiment, the first and second annular elements are connected by a separate connector member, such as between longitudinal struts to define another nesting feature as shown in FIG. 5. In yet another embodiment, a connector member extends between respective second angled struts of each of the first and second annular elements.

The nesting feature 187 is contoured for nestingly receiving one or more adjacent strut portions of the first or second sets in nested association therein when the stent is in the delivery configuration, as shown in FIG. 4. Some nesting features 187 nestingly receive a longitudinal strut 184 on opposite sides thereof generally parallel to the angled strut 183 in the contracted state, while other nesting features 187 nestingly receive the longitudinal struts 182 on opposite sides thereof at an angle to the angled strut 183 in the contracted state.

Figure 10:
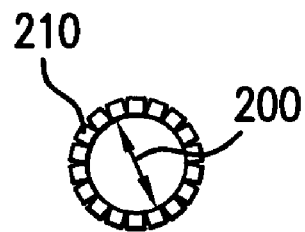
FIGS. 10-12 are cross-sectional views of different embodiments of single layer stents in a contracted position according to the invention.
Figure 11:
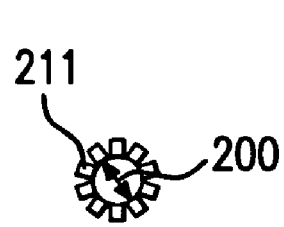
Figure 12:
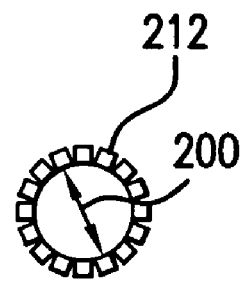

Referring to FIGS. 10-12, which are greatly simplified for purposes of illustration, various single-layer endoprosthesis having different numbers of strut members in an annular element are shown in cross-section in the delivery or compressed configuration. These figures are representative of certain stent embodiments known in the art, as well as embodiments in accordance with one aspect of the present invention, as described above. Stent 210 has eighteen struts in the cross-section shown, stent 211 has ten struts, and stent 212 has sixteen struts in an annular element. It is recognized that in stent patterns, the adjacent struts generally do not touch because the amount of movement (or how tightly the stent can be crimped or compressed) is limited by the strain in the metal or other material from which the stent is made. Generally, however, the inner diameter 200 of the contracted stent 210-212 is a function of the number of struts in the annular element and the widths of the strut members.

Figure 13:
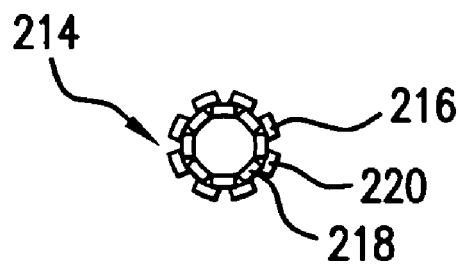
FIGS. 13 and 14 are cross-sectional views of an embodiment of a multilayer stent in accordance with another aspect of the invention in contracted and expanded states, respectively.
Figure 14:
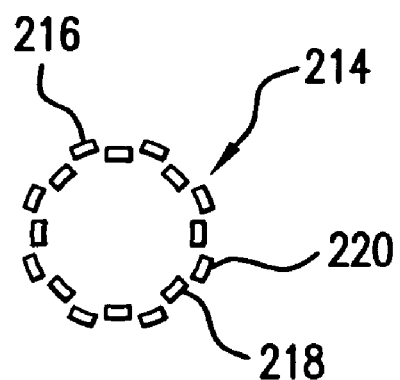

In accordance with another aspect of the invention, a multilayer endoprosthesis has a scaffolding body with inner and outer components that each include a set of interconnected strut members. The strut members of each set overlap the strut members of the other set to define a cooperating cell pattern. For example, and as shown in the embodiment of FIGS. 13 and 14, stent 214 includes multiple layers of struts 216, in which the struts 216 overlap each other as the stent is crimped or compressed to the delivery configuration. By providing multiple layers, the struts 216 can nest more tightly during crimping to enable the stent to crimp or compress to a smaller diameter while maintaining scaffolding characteristics similar to that of a single layer stent with an equal number of stents. That is, this embodiment provides a reduced profile stent without compromising the ability of the stent to support the vessel. A total of seventeen struts 216 are depicted in the embodiment shown of stent 216, although more or fewer can be provided.

The stent 216 preferably includes inner and outer components 218,220, each including a set of interconnected struts, preferably with about an equal number of struts. Preferably, struts of each set are interconnected to define corresponding annular elements capable of being moved between a delivery configuration and an expanded configuration, such as disclosed in the embodiments herein, or may be varied as desired for the particular application. The inner and outer components 218,220 are preferably separately manufactured as independent tubular members, each with about half (or other fraction depending on the embodiment) of the struts contemplated for the complete stent 216. The inner component 218 is preferably placed within the outer component 220 and attached thereto, such as at some or all of the points where the struts of the inner and outer components overlap in the expanded configuration. Preferably, the components 218,220 are attached directly to each other, without another material layer in between. In stents with more than two layers, preferably at least two of the layers that provide scaffolding or other supportive, expansive, or contractive structure are placed directly adjacent each other, without an intervening layer, and attached directly to each other as well.

Although a variety of stent patterns can be constructed with inner and outer components or layers, FIGS. 15-19 depict a representative embodiment of a stent having an arrowhead pattern defined by inner and outer components in accordance with the invention for purpose of illustration and not limitation. The annular element or set of strut members of inner stent component 222 shown in FIG. 15 includes a plurality of strut members interconnected in a zigzag manner to form an annular element. Each strut 226 has several strut portions 228 hingedly connected in a manner similar to that of the stent of FIGS. 1-3 above, but preferably extending in a double lightning-bolt pattern, as shown. Adjacent struts 226 are connected to form inner arrowheads 224. The apices 230 of these arrowheads 224 can be connected directly to longitudinally adjacent arrowheads 232 directly, as shown in dotted lines, or via connectors. Selected apices of the arrowheads can remain unconnected as desired. The annular element or set of strut members of the outer stent component 234 shown in FIG. 16 is embodied herein of substantially the same pattern as the strut members of the inner stent component 222, so as to form arrowheads 236.

The inner component is then positioned within the outer component and, preferably, affixed together. As shown in FIG. 17, the inner and outer stent components 222,234 are attached and preferably fixed together, with the strut members of each component 180° out of phase circumferentially, at points of overlap between the struts of each component, preferably forming hinges 238. The strut members of the attached stent components define double-sided arrowhead 240, each circumferential side of which belongs to a different one of the inner and outer stent components 222,234.

As shown in FIG. 18, when the complete multilayer stent 242 is crimped or contracted, the struts of each component 222,234 nests preferably only with other struts of the same component or layer, so as to be contracted to a diameter less than that of a single layer stent having the same number of struts as the two components combined. Referring to FIG. 19, portions of the inner and outer components 222,234 overlap radially when the stent 242 is contracted, permitting a reduced contracted diameter which can be easily delivered to a desired site and then expanded to a deployed configuration. As will be understood, other types of patterns can be made with inner and outer components or layers, including but not limited to arrowheads or quadrilateral areas as disclosed in the previous embodiments herein.

The multilayer embodiments of the invention can be constructed by making the components or layers separately and then assembling the components together. Local welds, clips, crimps, sutures or other techniques can be used to attach the layers together. The different layers of the endoprosthesis can be made with substantially different patterns to maximize or control stent performance. For example, one layer or component can be a coil-type structure to provide suitable strength without compromising flexibility, while the other layer or component can be a thin slotted tube for optimum scaffolding. Additionally, the different layers or components can be made of different materials chosen to optimize the performance of each layer. For example, the outer layer can be made of a NiTi alloy designed and set to provide a slight contractile force, such as just enough to engage the underlying layer. In this embodiment, the stent components need not be fixed, but may naturally press against each other to stabilize the multiple layers of the stent or the like.

In accordance with yet another aspect of the invention, an endoprosthesis can be provided, which generally can both self-contract and self-expand. Embodiments that can both constrain themselves on the delivery system and deploy themselves at the site of treatment can make it possible to reduce or eliminate a significant amount of material on the catheter or delivery system, thus allowing such a system to be used in more tortuous or smaller sized vessels. In the preferred examples of these embodiments, diameter-dependent competing mechanical forces within the endoprosthesis, such as a stent, are provided to cause the stent either to expand or to contract, depending on its diameter. Some parts of the stent are configured to exert contractive forces that tend to crimp or compress the stent, while other parts of the stent are configured to exert expansive forces that tend to deploy the stent. Both forces are generated through the particular patterns designed into each part of the stent.

For example, and in one embodiment, the geometry of the patterns is such that when the stent is at a low, contractive-dominant profile, such as in the delivery configuration, the contracting forces are dominant and the stent stays compressed, while when the stent is at least partially expanded to an expansive-dominant profile, the expansive forces become dominant and the stent expands, such as in the deployed configuration. In this manner, the delivery system need only require a thin balloon of minimum mass to deploy the stent from the contractive-dominant profile to the expansive-dominant profile, at which point the stent continues to expand on its own to its fully deployed diameter.

Alternatively, the stent can be designed such that the expansive forces are always dominant, but at the delivery configuration, the expansive forces are marginal, such that only a very thin sheath or other mechanism of minimal mass and volume need be used to constrain the stent. The expansive forces thus increase as the stent approaches the deployed configuration. In either case the assistive material, or stent deployment material of the delivery system, can be significantly thinner and less bulky than the traditional balloon-expandable or self-expanding stent delivery systems.

In accordance with one aspect of this invention, the stent is preferably made from a super elastic material, such as Nitinol or Elgiloy, to accommodate the changes in geometry employed for expansion without plastically deforming the material. In one embodiment, a stent with both contractile and expansive properties has two different competing geometries within the stent, one for each type of force. As used here, "geometry" is defined as being a cellular or sub-cellular pattern designed to provide a specific force-deformation characteristic. The stent as a whole may include both contractile and expansive sections, wherein each section includes one or more repeats of a particular geometry. The different super elastic sections are preferably heat set in the appropriate states: the contractile sections corresponding to the stent crimped or compressed in the delivery configuration, and the expansive sections corresponding to the stent expanded in a deployed configuration. The separately set sections can then be combined to form a stent in accordance with the invention.

The preferred self-crimping and expanding stent can employ different geometries for each section. To achieve the self-crimping-at-low-profile and self-expanding-at-high-profile function of the preferred embodiment described herein, the stent comprises regions of different strut geometries. Preferably, at least one of the geometries is configured such that its leverage or corresponding force is reduced as it is deformed from its set state, with an effect that counteracts and exceeds the increases in force caused by stress of the deformation from the set state.

Figure 20:
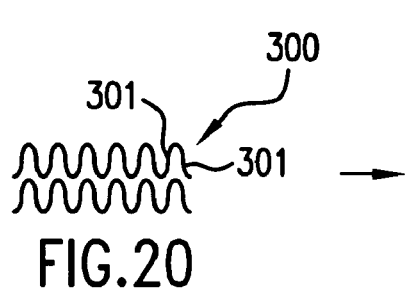
FIGS. 20-23 show simplified portions of typical stent scaffolding patterns in planar view.
Figure 21:
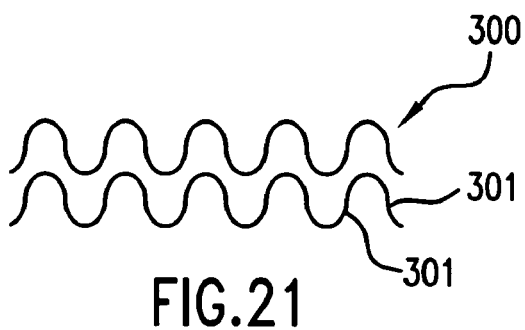
Figure 22:
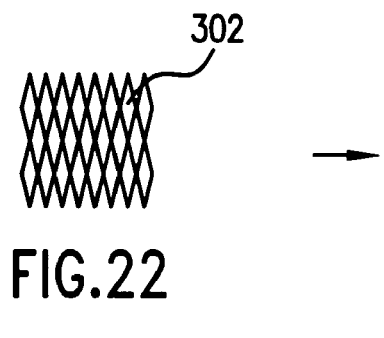
Figure 23:
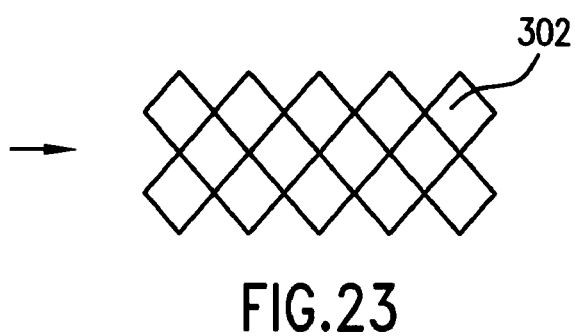

For example, the stent pattern subcomponent geometries shown in FIGS. 20 and 21 are made up of strut portions 301 and have a series of undulating bends 300 that unfold as the stent expands. The stent pattern subcomponents of FIGS. 22 and 23 have closed cells 302 that can contract or expand circumferentially. Pattern subcomponents of these types may be used for either the expansive or the contractile sections when made of super-elastic material and set separately as described above.

Figure 24:
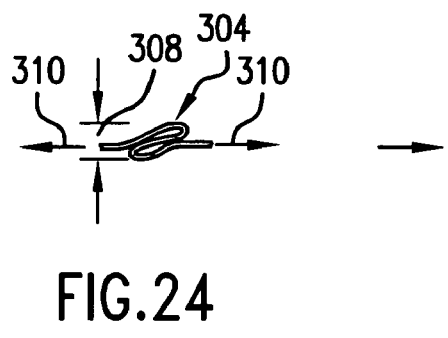
FIGS. 24-27 show planar views of simplified portions of other embodiments of stent scaffolding patterns that can be combined according with the invention.
Figure 25:
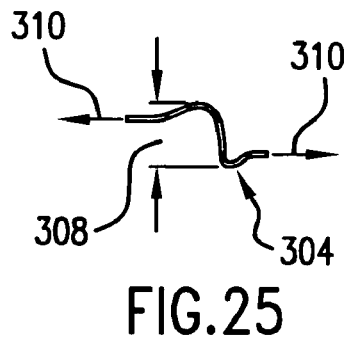
Figure 26:
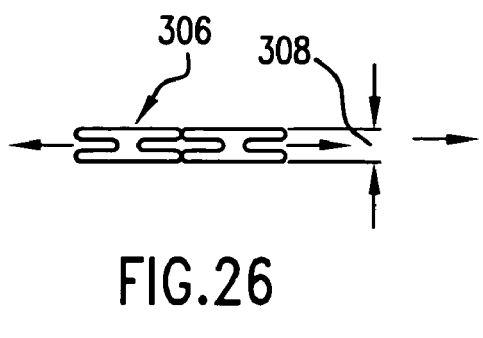
Figure 27:
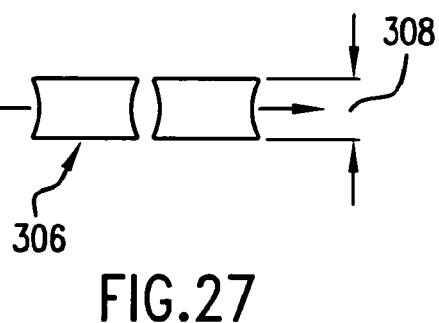

A preferred embodiment, however, incorporates the use of decreasing leverage patterns to enhance contractile forces. Examples of "decreasing leverage" pattern subcomponent 304,304 geometries are shown in FIGS. 24-27. As the stent expands, the lever arm 308 of the geometry increases with respect to the direction of force 310 applied circumferentially as shown in FIGS. 24 and 25 for one exemplary embodiment, and in FIGS. 26 and 27 for another exemplary embodiment. As the force 310 causes the bends of the geometry to open from a subcomponent contracted state to a subcomponent expanded state, the perpendicular distance from the direction of force to the bending point increases, thus increasing the lever arm 308. As the lever arm 308 increases, there is a point at which the expansion force 310 overcomes the opposing contraction force of the bends in the geometry. Conversely, in the portions of the geometry that make up contractile sections of the stent, as discussed below, the contraction force will overcome the force in the geometry that tends to expand the stent. Such decreasing leverage patterns can be made of super elastic material or deformable material.

Figure 28:
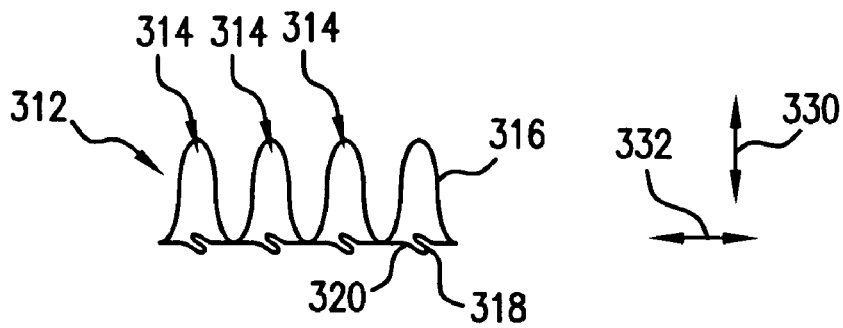
FIGS. 28-31 embodiments show portions of stent scaffolding patterns in planar view having expansive both and contractile sections.
Figure 29:
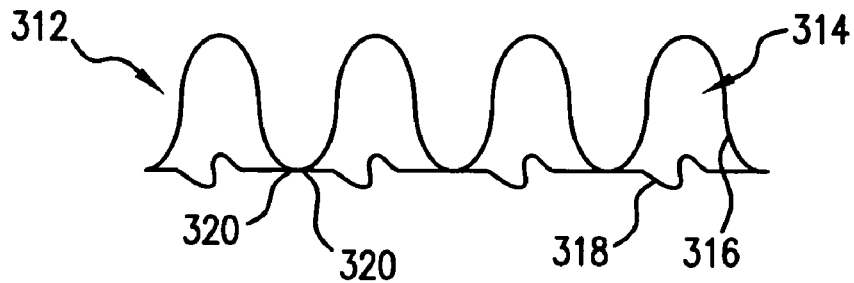
Figure 30:
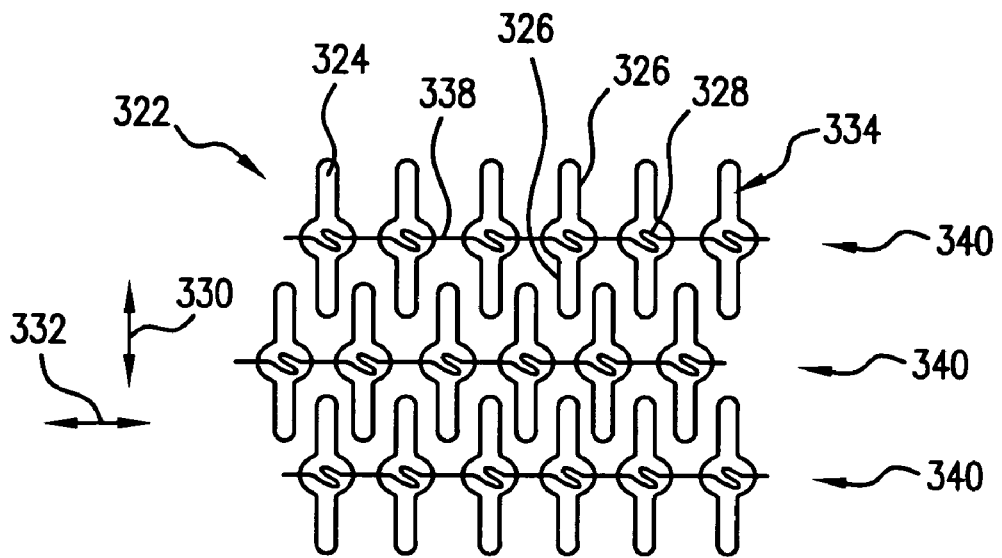
Figure 31:
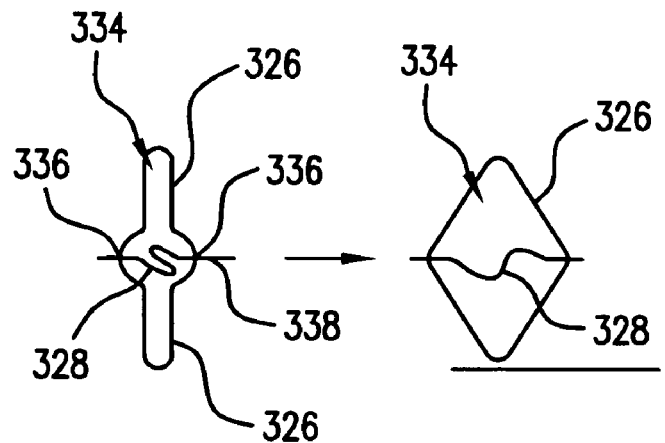

The annular element 312 shown in FIGS. 28 and 29 for purpose of illustration and not limitation has cells 314 that include expansive sections 316 fixed to contractile sections 318, preferably at hinge points 320. FIGS. 30 and 31 show another stent embodiment 322 with cells 324 that incorporate both expansive sections 326 and contractile sections 328 that are naturally biased opposite each other. In both of these embodiments, the expansive sections 316,326 preferably each have an elongated shape generally aligned in a longitudinal direction 330, and contractile sections 318,328 each have an S-shape or folded shape that extends generally in a circumferential direction 332. When moved from the contracted state to the expanded state, the expansive sections preferably expand circumferentially, and the contractile sections preferably expand circumferentially as well as longitudinally, with the S-shape uncoiling.

In the embodiment of FIGS. 30 and 31, the contractile sections 328 are contained within a closed cell defined between two expansive sections 326 that are oriented in opposite longitudinal directions. The contractile section 326 and both expansive sections 328 of each cell 334 are preferably connected at circumferentially opposite hinges 336, each of which hinge 336 connects to both struts from the expansive sections 326 and the strut from the contractile section. Connector struts 338 connect hinges 336 of circumferentially adjacent cells 334. Selected expansive sections 326 are connected to connector struts 338 extending longitudinally to longitudinally adjacent annular elements 340, such as by attaching to circumferential connectors 338.

Figure 32:
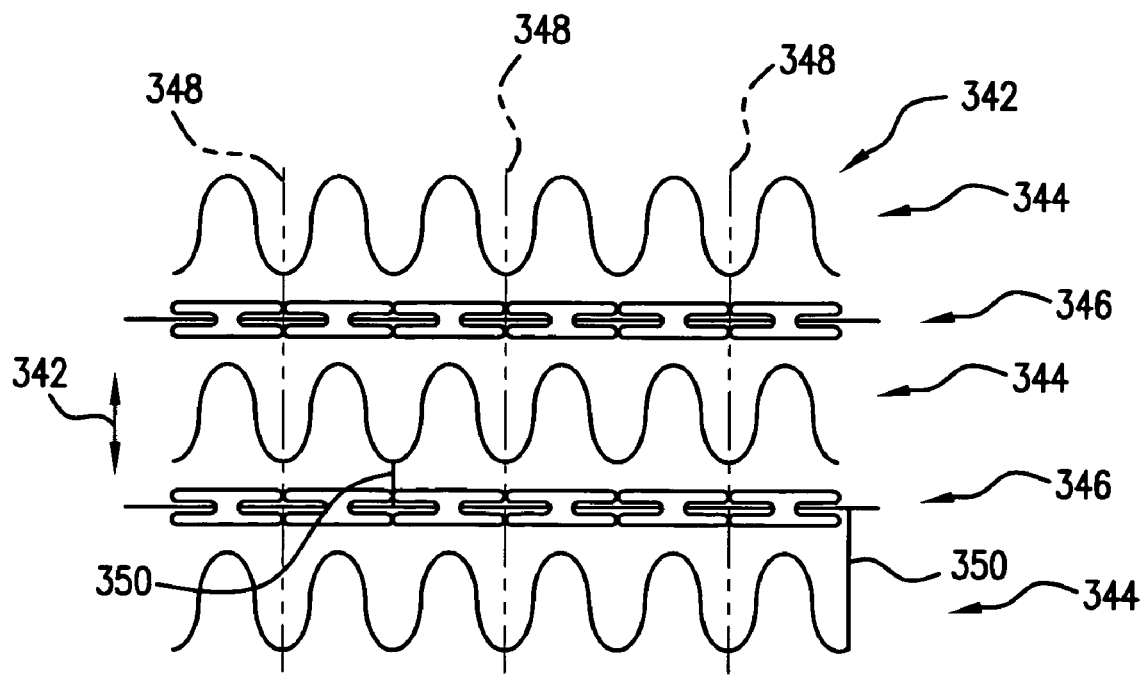
FIG. 32 is a planar view of a portion of a stent scaffolding structure having alternating rings of expansive and contractile patterns.

Referring to FIG. 32, stent 342 has expansive annular elements 344 and contractile annular elements 346, which are preferably disposed in alternating order along the longitudinal axis 346 of the stent 342, although other arrangements are possible. Preferably, a plurality of expansive or contractile annular elements are positioned circumferentially adjacent each other in the series to define annular elements of interconnecting struts as previously described. The expansive and contractile annular elements 344,346 are preferably coupled by longitudinal connectors 348 that preferably extend across several or all of the annular elements to provide a backbone linking the expansive and contractile forces. The backbone connectors 348 are preferably configured to maintain a generally even diameter of the stent in the expanded position, and preferably also in the contracted position. Other longitudinal connectors 350 can also or alternatively be used as desired for the performance of the particular stent. Connectors 350 preferably extend longitudinally along less than all of the annular elements and can connect to directly adjacent annular elements, while leaving the next longitudinally adjacent annular elements unconnected thereby.

Figure 33:
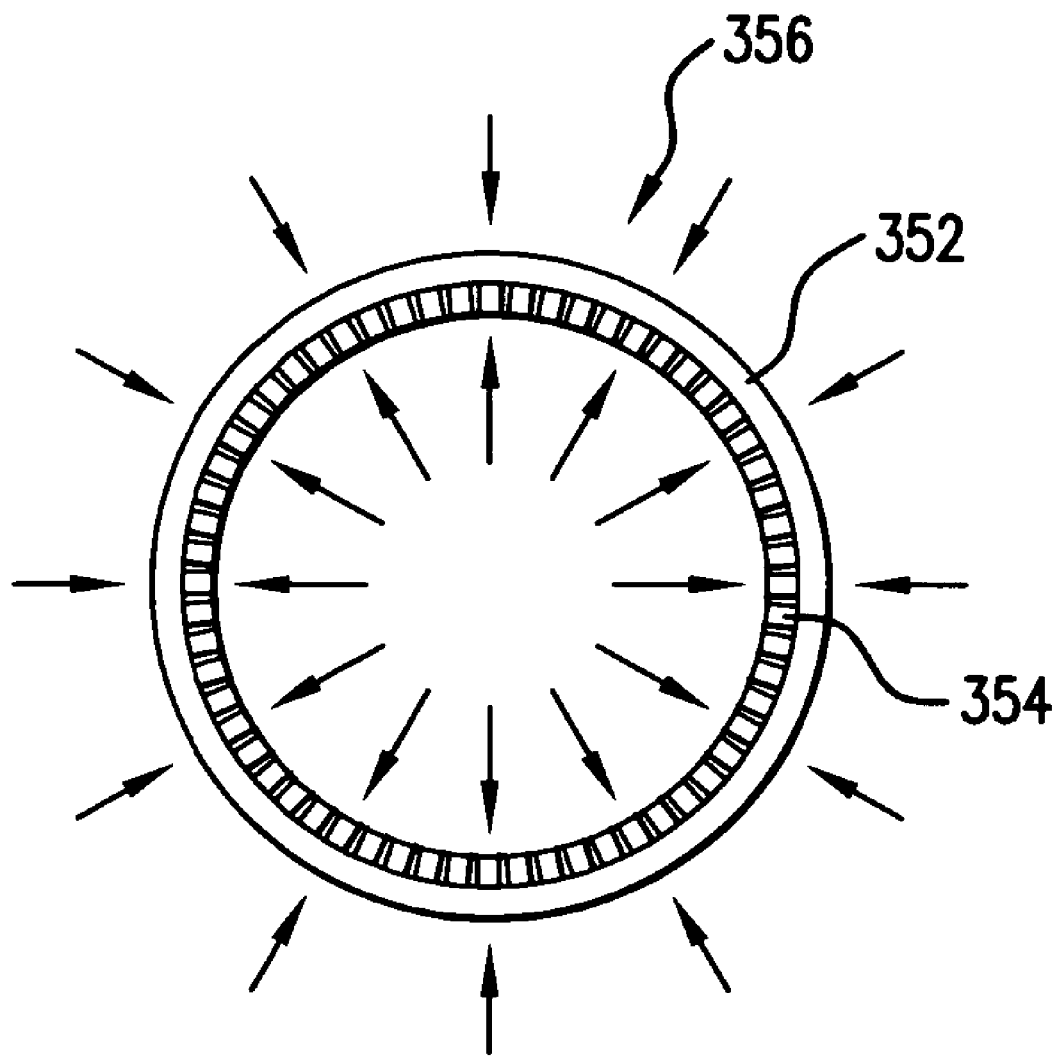
FIG. 33 is an axial diagrammatic view of a stent having both coaxial expansive and contractile layers.

The various subcomponents with the different geometries including those of FIGS. 1-3 and FIGS. 4-9 can be integrated to form a complete stent in several ways. The contractile or expansive properties can be alternated within a single piece of cut or etched material, making up the stent. This would result in a simple step of cutting and polishing, while the contractile and expansive sections of the stent would be set separately so that the contractile sections tend to contract the stent, and the expansive sections tend to expand the stent. The stent can also be built up from subassemblies of each section. As shown in FIG. 33, a multilayer stent 356 can be made up of two thin layers or stent components, with the outer layer 352 having the contractile pattern and the inner layer 354 having the expansive pattern. The inner and outer stent components can be attached or connected as described above in relation to and further in accordance with the multi-layered stent embodiments.

As noted above, the various aspects of the present invention allow for a variety of different endoprosthesis embodiments, based upon selective combinations of the features previously described and shown. Similarly, the endoprosthesis of the present invention can be made using any of a number of known manufacturing techniques and materials.

The material of construction is preferably selected according to the performance and biological characteristics desired. For example, the endoprosthesis of the invention can be made to be expanded by the change of a delivery condition, such as by the removal of a restraint or exposure to the environment within the body lumen, so as to be self expanding, or by the application of an external force or energy, such as by a balloon or by a radio frequency. For purpose of illustration and not limitation, embodiments of "self-expanding" and "balloon expandable" endoprostheses of the present invention are provided.

Self-expanding embodiments, or those that must be set, can be made from any of a variety of known suitable materials including super elastic or shape memory materials, such as nickel-titanium (NiTi) alloys, chromium alloys such as Elgiloy, or any equivalents thereof. An endoprosthesis made of a suitable super elastic material can be compressed or restrained in its delivery configuration on a delivery device using a sheath or similar restraint, and then deployed to its deployed configuration at a desired location by removal of the restraint as is known in the art. An endoprosthesis made of shape memory material generally can be delivered in a like manner, and if thermally sensitive, can be deployed by exposure of the endoprosthesis to a sufficient temperature to facilitate expansion as is known in the art. It also is possible to make the self-expanding embodiment of a biocompatible material capable of expansion upon exposure to the environment within the body lumen, such as a suitable hydrogel or hydrophilic polymer, including biodegradable or bioabsorbable polymers. For example, if made of an expandable hydrophilic material, the endoprosthesis can be delivered to the desired location in an isolated state, and then exposed to the aqueous environment of the body lumen to facilitate expansion. Alternative known delivery devices and techniques for a self-expanding endoprosthesis likewise can be used.

Balloon expandable embodiments or the like can be made of any of a variety of known suitable deformable materials, including stainless steel, silver, platinum, cobalt chromium alloys such as L605, MP35N or MP20N, or any equivalents thereof. "L605" is understood to be a trade name for an alloy available from UTI Corporation of Collegeville, Pa. including about 53% cobalt, 20% chromium and 10% nickel. "MP35N" and "MP20N" are understood to be trade names for alloys of cobalt, nickel, chromium and molybdenum available from Standard Press Steel Co., Jenkintown, Pa. MP35N generally includes about 35% cobalt, 35% nickel, 20% chromium, and 10% molybdenum. MP20N generally includes about 50% cobalt, 20% nickel, 20% chromium and 10% molybdenum. For delivery, the endoprosthesis of a suitable material is mounted in the delivery configuration on a balloon or similar expandable member of a delivery device. Once properly positioned within the body lumen at a desired location, the expandable member is expanded to expand the endoprosthesis to its deployed configuration as is known in the art. Additionally, or alternatively, balloon expandable embodiments can be made of suitable biocompatible polymers, including biodegradable or bioabsorbable materials, which are either plastically deformable or capable of being set in the deployed configuration. If plastically deformable, the material is selected to allow the endoprosthesis to be expanded in a similar manner using an expandable member so as to have sufficient radial strength and scaffolding and also to minimize recoil once expanded. If the polymer is to be set in the deployed configuration, the expandable member can be provided with a heat source or infusion ports to provide the catalyst to set or cure the polymer. Alternative known delivery devices and techniques for a self-expanding endoprosthesis likewise can be used.

Additional materials or compounds also can be incorporated into or on the endoprosthesis if desired. For example, the endoprosthesis can be provided with one or more coatings of biocompatible material to enhance the biocompatibility of the device. Such coatings can include hydrogels, hydrophilic and/or hydrophobic compounds, and polypeptides, proteins or amino acids or the like, such as PVP, PVA, parylene, and heparin. A preferred coating material includes phosphorylcholine, as disclosed in U.S. Pat. Nos. 5,705,583 and 6,090,901 to Bowers et al. and U.S. Pat. No. 6,083,257 to Taylor et al., each of which is incorporated by reference herein. Such coatings can also be provided on the endoprosthesis to facilitate the loading or delivery of beneficial agents or drugs, such as therapeutic agents, pharmaceuticals and radiation therapies. Alternatively, the surface of the endoprosthesis can be porous or include one or more reservoirs or cavities formed therein to retain beneficial agent or drug therein as is known in the art. For purposes of illustration and not limitation, the drug or beneficial agent can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors, as well as antineoplastics, antimitotics, antifibrins, antioxidants, agents that promote endothelial cell recovery, antiallergic substances, radiopaque agents, viral vectors, antisense compounds, oligionucleotides, cell permeation enhancers, and combinations thereof.

The endoprosthesis can also be provided with coverings, such as PTFE, ePTFE, Dacron, woven materials, cut filaments, porous membranes, or others materials to form a stent graft prosthesis. Similarly, a medical device, such as a valve, a flow regulator or monitor device, can be attached to the endoprosthesis, such that the endoprosthesis functions as an anchor for the medical device within the body lumen.

Additionally, an imaging compound or radiopaque material can be incorporated with the endoprosthesis. For example, one or more of the annular elements of the endoprosthesis can be made of a suitable radiopaque material, such as gold, tantalum or a similar material. Alternatively, the radiopaque material can be applied on selected surfaces of one or more of the annular elements using any of a variety of known techniques, including cladding, bonding, adhesion, fusion, deposition or the like. In a preferred embodiment, the material used for fabrication of at least a portion of the endoprosthesis includes a composite structure having multilayers of different materials or compositions. Generally, at least one layer is a base material such as stainless steel, nickel-titanium alloy or cobalt chromium alloy to impart the intended structural characteristic of the endoprosthesis, and at least another layer is a radiopaque material such as gold or tantalum for imaging purposes. For example, a tri-layer structure of 316L-Ta-316L is preferred for a balloon expandable stent and a tri-layer structure of NiTi-Ta-NiTi is preferred for a self-expanding stent. Suitable multi-layered composite structures are available in sheet or tube form from UTI Corporation of Collegeville, Pa., and are disclosed in U.S. Pat. No. 5,858,556, which is incorporated herein by reference. In yet another embodiment, one or more marker elements of radiopaque material can be attached to the endoprosthesis. For example, eyelets or tabs can be provided, preferably at at least a distal or proximal longitudinal end of the endoprosthesis. A rivet or bead of radiopaque material can then be attached to the eyelet or tab in a manner as known in the art. Alternatively, the separate marker can be attached directly to annular element. For example, and in accordance with a preferred embodiment of the invention, a wire or strip of radiopaque material can be wrapped around and secured to one or more nondeforming portions at one or both longitudinal ends of the endoprosthesis.

A variety of manufacturing techniques are well known and may be used for fabrication of the endoprosthesis of the present invention. For example, and in a preferred embodiment, the endoprosthesis can be formed from a hollow tube of suitable material using a known technique, such as by laser cutting, milling or chemical etching. The structure is then electropolished or otherwise finished to remove burrs and eliminate sharp edges and contaminates. Alternatively, the endoprosthesis can be fabricated from a sheet of suitable material using a similar cutting, milling or etching technique, and then rolled or bent about a longitudinal axis into the desired shape. If desired, the lateral edges of the structure can be joined together, such as by welding or bonding, to form a closed tubular structure, or the lateral edges can remain unattached to form an coiled, rolled sheet or open tubular structure. Conversely, a suitable material of construction can be applied selectively to a substrate to define the desired pattern of the endoprosthesis structure, and then the substrate can be removed. Other methods of manufacture also can be used for the endoprosthesis of the present invention, such as by bending toroidal rings or elongate lengths of wire into appropriately shaped members, such as that corresponding to each annular element, and then joining the appropriately shaped members together by a welding or bonding technique or the like. If a shape memory material is used, such as a nickel titanium alloy, the fabricated structure can be heat treated on a mandrel or the like using known techniques to establish the desired endoprosthesis shape and dimensions at a predetermined temperature, e.g. when above austenitic transition temperature.

As originally cut or fabricated, the endoprosthesis can correspond to its delivery configuration or a deployed configuration or a configuration therebetween. Preferably, however, the endoprosthesis is fabricated with a configuration at least slightly larger than the delivery configuration. In this manner, the endoprosthesis can be crimped or otherwise compressed into its delivery configuration on a corresponding delivery device. In another preferred embodiment, the endoprosthesis is originally fabricated from a tube having a diameter corresponding to the deployed configuration. In this manner, the longitudinally-free portions of the annular elements (e.g., apices not at a connection location) and circumferentially-free portions (e.g., the lateral sides of the arrowheads that are free) can be maintained within the general cylindrical shape (e.g., diameter) of the endoprosthesis when deployed, so as to avoid such portions from extending radially inwardly when in the deployed configuration. The endoprosthesis is therefore designed to match the target vessel in which the endoprosthesis is to be deployed. For example a stent will typically be provided with an outer diameter in the deployed configuration ranging from about 2 mm for neurological vessels to about 25 mm for the aorta. Similarly, a stent will typically be provided with a length ranging from 5 mm to 100 mm. Variations of these dimensions will be understood in the art based upon the intended application for the endoprosthesis.

As previously noted, the geometry of each part of the endoprosthesis, such as the width, thickness, length and shape of the strut members and other featured, as well as of the connectors if provided, is preferably selected to obtain predetermined expansion, flexibility, foreshortening, coverage scaffolding, and cross profile characteristics. For example, longer strut members can promote greater radial expansion or scaffolding coverage. The phase difference or circumferential alignment between adjacent annular elements likewise can be altered to control coverage and flexibility as well as facilitate more uniform drug delivery. Similarly, the number and placement of connection locations and, if present, the connectors, between longitudinally adjacent annular elements are preferably selected to obtained the desired flexibility of the endoprosthesis. The number of apices and other features can be varied to achieve desired performance characteristics.

While illustrative embodiments of the invention are disclosed herein, it will be appreciated that numerous modifications and other embodiments may be devised by those skilled in the art. For example, the various features of each embodiment may be altered or combined to obtain the desired stent characteristics. Therefore, it will be understood that the appended claims are intended to cover all such modifications and embodiments that come within the spirit and scope of the present invention.

What is claimed is:

1. An endoprosthesis, comprising
   a generally tubular scaffolding body configured to have a compressed diameter and an expanded diameter,
   the body having a first subcomponent having a first geometry and defining a first bias when in a first range of diameter between the compressed and expanded diameters, the body having a second subcomponent having a second geometry different from the first geometry, the second subcomponent defining a second bias when in a second range of diameter between the first range and the expanded diameter, wherein the second bias is expansive and has a greater expansive magnitude than the first bias.

2. The endoprosthesis of claim 1, wherein the first bias is contractive.

3. The endoprosthesis of claim 2, wherein one of the first and second subcomponents of the body define a contractile portion that is biased to contract the body and the other of the first and second subcomponents define an expansive portion that is biased to expand the body.

4. The endoprosthesis of claim 3, wherein the contractile portion is disposed within the expansive portion.

5. The endoprosthesis of claim 3, wherein the contractile portion and expansive portion are disposed in longitudinally adjacent annular elements of the body.

6. The endoprosthesis of claim 5, wherein body comprises a plurality of longitudinal connectors coupling a plurality of the adjacent annular elements.

7. The endoprosthesis of claim 6, wherein at least one of the longitudinal connectors extends across at least three adjacent annular elements.

8. The endoprosthesis of claim 3, wherein the one of the contractile and extensive portions comprises an outer tubular structure, and the other comprises an inner tubular structure received coaxially within the outer tubular structure.

9. The endoprosthesis of claim 8, wherein the contractile portion comprises the outer tubular structure, and the expansive portion comprises the inner tubular structure.

10. The endoprosthesis of claim 3, wherein the contractile portion has a geometry for decreasing the leverage of the bias thereof when the body is expanded.

11. The endoprosthesis of claim 3, wherein the expansive portion has a geometry for increasing the leverage of the bias thereof when the body is expanded.

12. The endoprosthesis of claim 11, wherein the contractile portion has a geometry for decreasing the leverage of the bias thereof when the body is expanded.

13. The endoprosthesis of claim 1, wherein the endoprosthesis is a stent.

* * * * *